(12) United States Patent
Hogan

(10) Patent No.: US 9,840,731 B2
(45) Date of Patent: Dec. 12, 2017

(54) PRESERVATION OF BIOLOGICAL MATERIALS IN NON-AQUEOUS FLUID MEDIA

(71) Applicant: GenTegra, LLC, Pleasanton, CA (US)

(72) Inventor: Michael Hogan, Tucson, AZ (US)

(73) Assignee: Gentegra, LLC, Pleasanton, CA (US)

( * ) Notice: Subject to any disclaimer, the term of this patent is extended or adjusted under 35 U.S.C. 154(b) by 480 days.

(21) Appl. No.: 14/213,066

(22) Filed: Mar. 14, 2014

(65) Prior Publication Data

US 2015/0267245 A1 Sep. 24, 2015

Related U.S. Application Data

(60) Provisional application No. 61/786,171, filed on Mar. 14, 2013.

(51) Int. Cl.
*C12Q 1/68* (2006.01)

(52) U.S. Cl.
CPC ......... *C12Q 1/6806* (2013.01); *C12Q 1/6802* (2013.01); *C12Q 1/686* (2013.01); *C12Q 2527/125* (2013.01)

(58) Field of Classification Search
CPC .................................................. C12Q 1/6806
USPC ........... 536/23.1; 530/300; 422/430; 435/6.1
See application file for complete search history.

(56) References Cited

U.S. PATENT DOCUMENTS

| | | |
|---|---|---|
| 2004/0092470 A1 | 5/2004 | Leonard et al. |
| 2006/0147944 A1 | 7/2006 | Chomczynski |
| 2010/0173295 A1 | 7/2010 | Lenz et al. |
| 2011/0224419 A1* | 9/2011 | Himmelreich ..... C12N 15/1006 536/25.41 |
| 2012/0100522 A1 | 4/2012 | Saghbini et al. |

OTHER PUBLICATIONS

International Bureau, "Search Report and Written Opinion," issued in connection with International Patent Application No. PCT/US14/28693, dated Nov. 12, 2014, 8 pages.
International Bureau, "International Preliminary Report on Patentability," issued in connection with International Patent Application No. PCT/US14/28693, dated Oct. 22, 2015, 7 pages.

* cited by examiner

*Primary Examiner* — Jezia Riley
(74) *Attorney, Agent, or Firm* — McKee, Voorhees & Sease, PLC

(57) ABSTRACT

The invention provides compositions and methods for preserving a biological material—such as a protein, a nucleic acid or a biological sample, or any combination thereof—in a substantially water-free, nonionic or ionic organic solvent. Improved preservation, including for example the stability and/or the solubility of the biological material in the substantially water-free fluid medium, is achieved with compositions comprising one or more substances (e.g., an antioxidant) described in the disclosure, and/or a metal salt. The biological material is soluble and stable, and retains its function and activity, when it is preserved in the substantially water-free fluid medium at ambient temperature or higher for extended periods of time. Therefore, the composition comprising the biological material does not need to be refrigerated or frozen during shipping or storage.

19 Claims, 7 Drawing Sheets

PRESERVATION OF BIOLOGICAL MATERIALS IN NON-AQUEOUS FLUID MEDIA

CROSS-REFERENCE TO RELATED APPLICATIONS

This application claims priority under 35 U.S.C. §119 of a provisional application Ser. No. 61/786,171 filed Mar. 14, 2013, which is hereby incorporated by reference in its entirety.

GRANT REFERENCE

This invention was made with government support under Contract No. HR0011-12-C-0005 awarded by the Defense Advanced Research Projects Agency (DARPA). The government has certain rights in the invention.

FIELD OF THE INVENTION

The present invention relates to preservation of biological materials, such as proteins, nucleic acids and biological samples, in substantially water-free fluid media.

BACKGROUND OF THE INVENTION

Biological materials, such as proteins and nucleic acids, may in certain instances be freeze dried (lyophilized) to enhance their stability in the absence of refrigeration. Freeze-drying comprises freezing of an aqueous mixture containing a biological material and removal of water via sublimation. Biological materials can suffer denaturation—including for example, partial denaturation—as a result of freeze-drying, for example, as a result of the freezing step and/or the sublimation step. Thus, there is a need in the art for methods, compositions, and systems for stable preservation of biological materials that prevents denaturation.

SUMMARY OF THE INVENTION

It is therefore a primary object, feature, and/or advantage of the present invention to improve on or overcome the deficiencies in the art.

It is another object, feature, and/or advantage of the present invention to provide methods for preservation of biological materials, such as proteins, nucleic acids and biological samples, in substantially water-free fluid media.

It is another object, feature, and/or advantage of the present invention to provide methods for preservation of biological materials, wherein the biological materials are soluble and stable in the substantially water-free fluid media at ambient temperature or higher for extended periods of time, and thus do not need to be refrigerated or frozen during shipping or storage.

It is another object, feature, and/or advantage of the present invention to provide methods of preserving biological material in a non-aqueous fluid media, including, for example, a non-ionic organic solvent such as an alcohol solvent or an ionic organic solvent comprising an organic salt and an organic hydrogen bond donor to produce an aqueous organic mixture.

It is another object, feature, and/or advantage of the present invention to provide compositions for preservation of biological materials, such as proteins, nucleic acids and biological samples, in substantially water-free fluid media.

It is another object, feature, and/or advantage of the present invention to provide compositions for preservation of biological materials, wherein the biological materials are soluble and stable in the substantially water-free fluid media at ambient temperature or higher for extended periods of time, and thus do not need to be refrigerated or frozen during shipping or storage.

In one aspect, the present invention provides methods and compositions for preservation of biological materials, such as proteins, nucleic acids and biological samples, in substantially water-free fluid media. The biological materials are soluble and stable in the substantially water-free fluid media at ambient temperature or higher for extended periods of time, and thus do not need to be refrigerated or frozen during shipping or storage. The biological materials retain their structural integrity, function and activity after preservation in the substantially water-free fluid media at ambient temperature or higher for extended periods of time. Because the biological materials are preserved in a fluid medium, they may not need to be re-dissolved for use in fluid-phase reactions or assays, including nucleic acid amplification reactions based on polymerase chain reaction (PCR) and analytical and diagnostic assays, such as immunoassays.

In one aspect, the present invention provides compositions comprising a biological material in a substantially water-free fluid medium, wherein the fluid medium comprises a non-ionic organic solvent (e.g., an alcohol solvent) or an ionic organic solvent comprising an organic salt and an organic hydrogen bond donor. To enhance, e.g., the stability and/or the solubility of the biological material in the substantially water-free fluid medium, the compositions can further comprise a metal salt, and/or one or more substances selected from the group consisting of reducing agents, antioxidants, free radical scavengers, oxygen radical scavengers, hydroxyl radical scavengers, singlet oxygen quenchers, hydroperoxide-removing agents, protease inhibitors, nuclease inhibitors, ribonuclease (RNase) inhibitors, deoxyribonuclease (DNase) inhibitors, metal chelators, preservatives, anti-microbials, buffers (or buffering agents), detergents, and chaotropes.

In another aspect, the present invention provides methods of preserving a biological material, comprising mixing an aqueous mixture comprising a biological material with a non-ionic organic solvent (e.g., an alcohol solvent) or an ionic organic solvent comprising an organic salt and an organic hydrogen bond donor to produce an aqueous organic mixture, and removing water from the aqueous organic mixture to produce a substantially water-free fluid medium comprising the biological material and the non-ionic or ionic organic solvent. The fluid medium can further comprise a metal salt and/or one or more substances as described herein.

In another aspect, the present invention provides containers and kits containing compositions that comprise biological materials in substantially water-free fluid media.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION OF THE INVENTION

Figure 1:
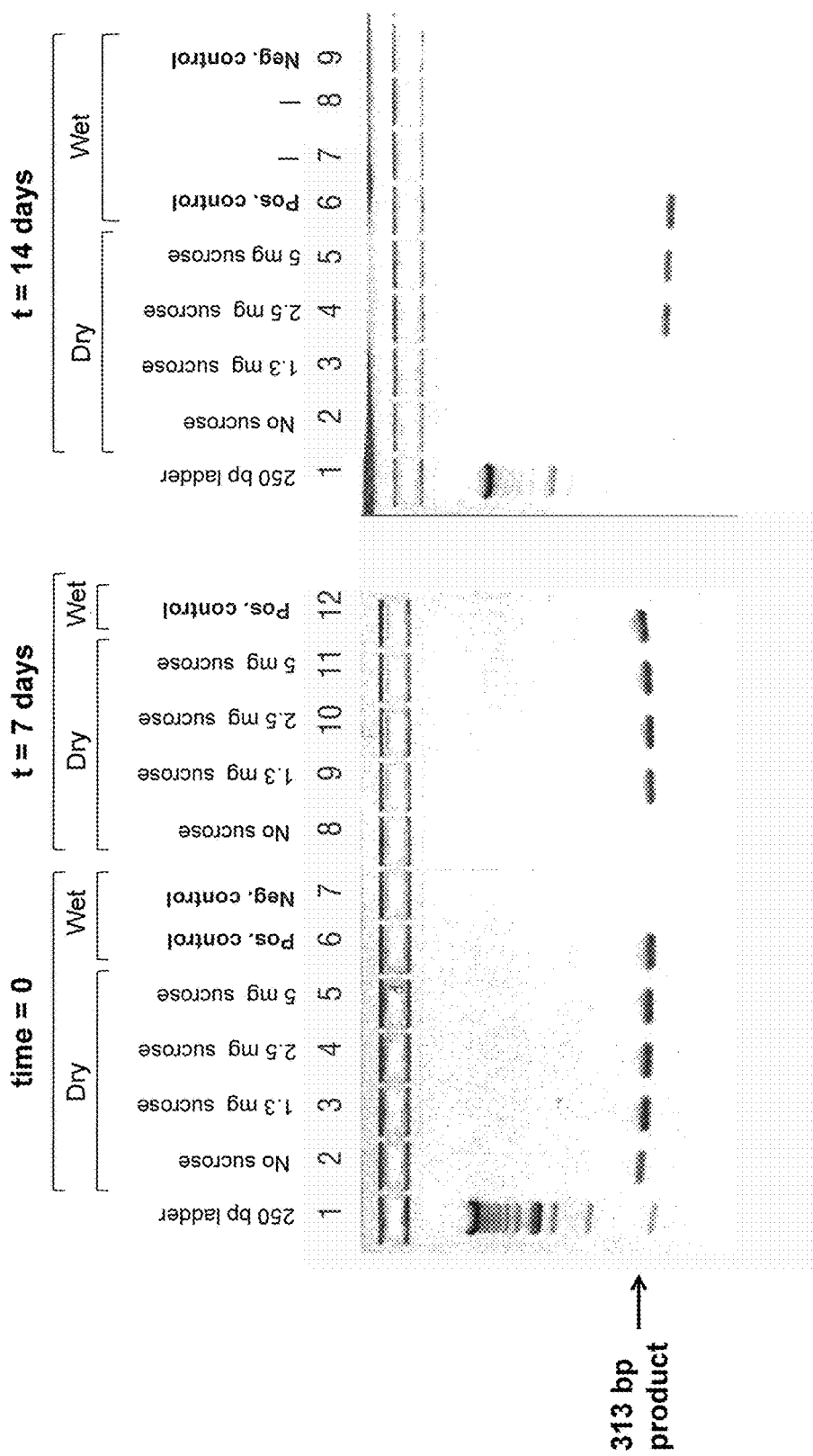
FIG. 1 shows electrophoresis results of reverse transcription PCR (RT-PCR) for analysis of human 18S ribosomal RNA (rRNA) after preservation of RT-PCR reagents in glycerol, with addition of no sucrose or varying amounts of sucrose, at ambient temperature for varying periods of time.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein may be employed in practicing the disclosure. It is further understood that every embodiment of the disclosure may optionally be combined with any one or more of the other embodiments described herein which are consistent with that embodiment.

Headings are included herein for reference and to aid in locating certain sections. Headings are not intended to limit the scope of the embodiments and concepts described in the sections under those headings, and those embodiments and concepts may have applicability in other sections throughout the entire disclosure.

All patent literature and all non-patent literature cited herein are incorporated herein by reference in their entirety to the same extent as if each patent literature or non-patent literature were specifically and individually indicated to be incorporated herein by reference in its entirety.

The term "exemplary" as used herein means "serving as an example, instance, or illustration". Any embodiment characterized herein as "exemplary" is not necessarily to be construed as preferred or advantageous over other embodiments.

Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values. In certain embodiments, the term "about" or "approximately" means within 10% or 5% of the specified value.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

Percentage of a substance by mass is understood to refer to the amount of a component or portion of a combined or entire composition in reference to the amount represented by the combined or entire composition. For example, if a fluid is 10% water by mass, it is understood that the water represents 10% of the mass represented by the entire fluid, including the water.

In some embodiments, the term "ambient temperature" or "room temperature" refers to a temperature range from about 18° C. to about 27° C., or from about 20° C. to about 25° C., or from about 22° C. to about 25° C. In other embodiments, the term "ambient temperature" or "room temperature" refers to a temperature of about 18° C., 19° C., 20° C., 21° C., 22° C., 23° C., 24° C., 25° C., 26° C. or 27° C. In certain embodiments, the term "ambient temperature" or "room temperature" refers to a temperature of about 22° C., 23° C., 24° C. or 25° C.

The term "halide" refers to fluoride, chloride, bromide and iodide.

The terms "biological reaction" and "biochemical reaction" are used interchangeably herein unless expressly indicated otherwise.

In one embodiment, the invention provides for preservation of biological materials in substantially water-free fluid media. The term "biological materials" refers to naturally occurring molecules and substances such as proteins, nucleic acids and biological samples, or man-made equivalents or homologues thereof. Examples of polypeptide biological materials include, but are not limited to, enzyme that mediate a nucleic acid reaction, polypeptides that regulate an enzyme, antibodies, polypeptide ligands of antibodies, polypeptide aptamers, proteins or enzymes useful for detection, toxins, hormones, cytokines, polypeptide therapeutics, or vaccines, and derivatives of any of these. Examples of nucleic acid biological materials include, but are not limited to polynucleotides used in a nucleic acid reaction, catalytic polynucleotides, or polynucleotides that binds specifically to a target ligand, and derivatives of any of these. Examples of biological sample biological materials include, but are not limited to, biological fluids, biological suspensions, fluid aspirates, blood, plasma, serum, lymph, cerebrospinal fluid, gastric fluid, bile, perspiration, ocular fluid, tears, oral fluid, sputum, saliva, buccal samples, tonsil samples, nasal samples, mucus, nasopharyngeal samples, semen, urine, vaginal samples, cervical samples, rectal samples, fecal samples, wound or purulent samples, hair, tissue, tissue homogenates, cells, cellular lysate, tissue or cell biopsy, skin cells, tumor or cancer cells, microbes, pathogens, bacteria, fungi, protozoa, and viruses.

A biological material can be transferred from an aqueous medium to a substantially water-free fluid medium without passing through an intermediate solid state (e.g., without freezing the aqueous medium or an aqueous organic medium), by mixing of an aqueous mixture comprising the biological material with a non-ionic organic solvent (e.g., an alcohol solvent) or an ionic organic solvent and removal of water from the resulting aqueous organic mixture. Removal of water may be achieved using any number of solvent removal techniques known in the art, including, for example, distillation and evaporation. In a preferred embodiment, water removal comprises evaporation. Evaporation process and techniques include, for example, open-dish or open-container evaporation, reduced-pressure evaporation, and rotary evaporation.

To enhance, e.g., the stability and/or the solubility of the biological material in the substantially water-free fluid medium, the fluid medium can comprise a metal salt, and/or one or more substances selected from the group consisting of reducing agents, antioxidants, free radical scavengers, oxygen radical scavengers, hydroxyl radical scavengers, singlet oxygen quenchers, hydroperoxide-removing agents, protease inhibitors, nuclease inhibitors, ribonuclease (RNase) inhibitors, deoxyribonuclease (DNase) inhibitors, metal chelators, preservatives, anti-microbials, buffers (or buffering agents), detergents, and chaotropes.

The biological materials are soluble and stable in the substantially water-free fluid media at ambient temperature or higher for extended periods of time, and thus do not need to be refrigerated or frozen during shipping or storage. In addition, the biological materials retain their structural integrity, function and activity after preservation in the substantially water-free fluid media at ambient temperature or higher for extended periods of time. The biological materials retain their structural integrity, function and activity even though alcohol solvents (including polyol solvents) and ionic organic solvents (including deep eutectic solvents) comprising an organic salt and an organic hydrogen bond donor can denature biological materials such as proteins (including enzymes) and nucleic acids (including double-stranded DNA). Furthermore, the biological materials retain their structural integrity, function and activity even though removal of water from an aqueous organic mixture comprising a biological material (e.g., a protein, such as an enzyme) and a salt (e.g., an inorganic salt, such as sodium chloride) can result in, e.g., at least a 5-fold or 10-fold greater concentration of the salt in the substantially water-free fluid medium, which high salt concentration may be expected to be deleterious to the structure, function and/or activity of the biological material.

In addition to avoiding denaturation that can result from freeze-drying of biological materials, preservation of biological materials in substantially water-free fluid media can facilitate handling of the biological materials. Unlike lyophilized biological materials, because the biological materials of the present disclosure are preserved in a fluid medium, they may not need to be re-dissolved for use in fluid-phase reactions or assays, including nucleic acid amplification reactions based on PCR and analytical and diagnostic assays, such as immunoassays.

Compositions Comprising a Biological Material in an Anhydrous, Non-Ionic Organic Solvent Some embodiments of the disclosure relate to compositions comprising a biological material in a substantially water-free, non-ionic organic solvent (e.g., an alcohol solvent). In certain embodiments, such a composition comprises a polypeptide, a polynucleotide or a biological sample, or any combination thereof, and at least one alcohol solvent. In one aspect the polypeptide may be, for example, an enzyme that mediates a nucleic acid reaction, a polypeptide that regulates an enzyme, an antibody, a polypeptide ligand of an antibody, a polypeptide aptamer, a protein or enzyme useful for detection, a toxin, a hormone, a cytokine, a polypeptide therapeutic or a vaccine, or a derivative thereof or any combination thereof. In another aspect the polynucleotide may be, for example, a polynucleotide used in a nucleic acid reaction, a catalytic polynucleotide, or a polynucleotide that binds specifically to a target ligand, or a derivative thereof or any combination thereof. In another aspect the biological sample may be, for example, a biological fluid, a biological suspension, a fluid aspirate, blood, plasma, serum, lymph, cerebrospinal fluid, gastric fluid, bile, perspiration, ocular fluid, tears, oral fluid, sputum, saliva, a buccal sample, a tonsil sample, a nasal sample, mucus, a nasopharyngeal sample, semen, urine, a vaginal sample, a cervical sample, a rectal sample, a fecal sample, a wound or purulent sample, hair, a tissue, a tissue homogenate, cells, a cellular lysate, a tissue or cell biopsy, skin cells, tumor or cancer cells, a microbe, a pathogen, a bacterium, a fungus, a protozoan or a virus, or any combination thereof.

In another aspect, the alcohol solvent may be selected from the group consisting of linear and branched C2-C6 acyclic alcohols having one or more hydroxyl groups and C3-C6 cyclic alcohols having one or more hydroxyl groups and three to six ring carbon atoms. The acyclic alcohols and cyclic alcohols optionally comprise one or more halide atoms. In a preferred embodiment, the composition is in a fluid state and is substantially free of water.

In some embodiments, the at least one alcohol solvent in the composition comprises no more than about 20%, 15%, 10%, 5%, 4%, 3%, 2%, 1% or 0.5% water by mass, relative to the combined mass of water and the at least one alcohol solvent, e.g., after storage of the composition in a closed container at a temperature from ambient temperature to about 40° C. for at least about 1 day, 3 days, 1 week, 2 weeks, 3 weeks, 1 month, 2 months, 3 months, 6 months, 1 year, 1.5 years or 2 years. The closable or closed container may be, for example, a capped tube, vial or well. In certain embodiments, the at least one alcohol solvent in the composition comprises no more than about 10%, 5% or 1% water by mass after storage of the composition in a closed container at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In some embodiments, the at least one alcohol solvent in the composition comprises no more than about 10%, 5% or 1% water by mass relative to the combined mass of water and the at least one alcohol solvent after storage of the composition in a closed container at ambient temperature for at least about 3 months or 6 months.

In further embodiments, the at least one alcohol solvent is substantially soluble in water—for example, at least about 50%, 60%, 70%, 80%, 90%, 95% or 99% of the at least one alcohol solvent by mass or volume is soluble in water. In certain embodiments, at least about 90%, 95% or 99% of the at least one alcohol solvent by mass or volume is soluble in water. In an embodiment, the at least one alcohol solvent is miscible with water. Solubility of the at least one alcohol solvent in water promotes transfer of a biological material from an aqueous medium to the at least one alcohol solvent.

In yet further embodiments, the at least one alcohol solvent has a boiling point substantially greater than that of water—e.g., a boiling point at least or greater than about 110° C., 125° C., 150° C., 175° C., 200° C. or 250° C. at a pressure of about 1 atmosphere (atm). In certain embodiments, the at least one alcohol solvent has a boiling point at least or greater than about 150° C., 175° C. or 200° C. at a pressure of about 1 atm. The at least one alcohol solvent having a boiling point greater than the boiling point of water allows for an aqueous mixture comprising a biological material to be mixed with at least one alcohol solvent and for water to be selectively removed (e.g., by evaporation) from the resulting aqueous organic mixture without substantial loss of the at least one alcohol solvent.

In additional embodiments, the at least one alcohol solvent may have a dynamic (or absolute) viscosity of no more than about 1500, 1000, 500, 400, 300, 200, 100, 50 or 25 centipoise (cP) or mPa·s at ambient temperature. In certain embodiments, the at least one alcohol solvent has a dynamic (or absolute) viscosity of no more than about 1000, 500, 200, 100 or 50 cP or mPa·s at ambient temperature. A lower dynamic (or absolute) viscosity of the at least one alcohol solvent allows for more facile handling of the composition comprising the biological material and the at least one alcohol solvent (e.g., using a pipette or other means of transferring the fluid composition).

In some embodiments, the linear and branched C2-C6 acyclic alcohols having one or more hydroxyl groups and optionally comprising one or more halide atoms are linear and branched C2-C5 acyclic alcohols having one hydroxyl group and optionally comprising one or more halide atoms. Non-limiting examples of linear and branched C2-C5 acyclic alcohols having one hydroxyl group and optionally comprising one or more halide atoms include 2-chloroethanol, 2,2-dichloroethanol, 1-butanol, 1-pentanol, 2-methylbutan-1-ol, 3-methylbutan-1-ol, 2,2-dimethylpropan-1-ol, pentanol, 3-methylbutan-2-ol, and 3-pentanol.

In other embodiments, the linear and branched C2-C6 acyclic alcohols are linear and branched C2-C6 acyclic alcohols having two or more (e.g., two or three) hydroxyl groups and optionally comprising one or more halide atoms. Non-limiting examples of linear and branched C2-C6 acyclic alcohols having two or more (e.g., two or three) hydroxyl groups and optionally comprising one or more halide atoms include 1,2-ethanediol (ethylene glycol), 1,2-propanediol (propylene glycol), 1,3-propanediol, 1,2,3-propanetriol (glycerol), 1,2-butanediol, 1,3-butanediol, 1,4-butanediol, 2,3-butanediol, 1,2,3-butanetriol, 1,2,4-butanetriol, 1,2-pentanediol, 1,3-pentanediol, 1,4-pentanediol, 1,5-pentanediol, 2,3-pentanediol, 2,4-pentanediol, 1,2,3-pentanetriol, 1,2,4-pentanetriol, 1,2,5-pentanetriol, 1,3,4-pentanetriol, 1,3,5-pentanetriol, 2,3,4-pentanetriol, 1,2-hexanediol, 1,3-hexanediol, 1,4-hexanediol, 1,5-hexanediol, 2,3-hexanediol, 2,4-hexanediol, 2,5-hexanediol, 3,4-hexanediol, di(ethylene glycol), and tri(ethylene glycol).

In certain embodiments, the linear and branched C2-C6 acyclic alcohols are linear and branched C2-C5 acyclic alcohols having two or more (e.g., two or three) hydroxyl groups and optionally comprising one or more halide atoms. In some embodiments, the at least one alcohol solvent comprises ethylene glycol, 1,2-propanediol, 1,3-propanediol, glycerol, 1,2-butanediol, 1,3-butanediol, 1,4-butanediol, 2,3-butanediol, 1,2,4-butanetriol or 1,5-pentanediol, or any combination thereof. In certain embodiments, the at least one alcohol solvent comprises ethylene glycol, 1,3-propanediol, glycerol or 1,2-butanediol, or any combination thereof.

In some embodiments, the C3-C6 cyclic alcohols having one or more hydroxyl groups and optionally comprising one or more halide atoms are C4 or C5 cyclic alcohols having one or more hydroxyl groups and four or five ring carbon atoms and optionally comprising one or more halide atoms. In certain embodiments, the at least one alcohol solvent comprises cyclobutanol or cyclopentanol, or both.

In some embodiments, the at least one alcohol solvent comprises two or more alcohol solvents. In certain embodiments, the at least one alcohol solvent comprises two or more alcohol solvents selected from the group consisting of ethylene glycol, 1,2-propanediol, 1,3-propanediol, glycerol, 1,2-butanediol, 1,3-butanediol, 1,4-butanediol, 2,3-butanediol, 1,2,4-butanetriol, and 1,5-pentanediol. In additional embodiments, the at least one alcohol solvent comprises: (a) ethylene glycol and glycerol; or (b) ethylene glycol and 1,2-butanediol; or (c) glycerol and 1,2-butanediol. In further embodiments, the at least one alcohol solvent comprises glycerol and an additional alcohol solvent that can be any alcohol solvent described herein. In certain embodiments, the at least one alcohol solvent comprises glycerol and an additional alcohol solvent selected from the group consisting of ethylene glycol, 1,2-propanediol, 1,3-propanediol, 1,2-butanediol, 1,3-butanediol, 1,4-butanediol, 2,3-butanediol, 1,2,3-butanetriol, 1,2,4-butanetriol, 1,2-pentanediol, 1,3-pentanediol, 1,4-pentanediol, 1,5-pentanediol, 2,3-pentanediol, 2,4-pentanediol, 1,2,3-pentanetriol, 1,2,4-pentanetriol, 1,2,5-pentanetriol, 1,3,4-pentanetriol, 1,3,5-pentanetriol, 2,3,4-pentanetriol, 1,2-hexanediol, 1,3-hexanediol, 1,4-hexanediol, 1,5-hexanediol, 2,3-hexanediol, 2,4-hexanediol, 2,5-hexanediol, 3,4-hexanediol, di(ethylene glycol), and tri(ethylene glycol).

In some embodiments, the composition comprises an enzyme. In certain embodiments, the enzyme mediates a nucleic acid reaction. In some embodiments, the enzyme that mediates a nucleic acid reaction comprises a topoisomerase, a helicase, a DNA polymerase, a reverse transcriptase, an RNA polymerase, a DNA ligase, an RNA ligase, a DNA repair enzyme, an RNA repair enzyme, an endonuclease, an exonuclease, a deoxyribonuclease (DNase), a ribonuclease (RNase), a transposase, a restriction enzyme or a nicking enzyme, or any combination thereof. In further embodiments, the enzyme that mediates a nucleic acid reaction comprises a DNA polymerase, a reverse transcriptase or an RNA polymerase, or any combination thereof. In certain embodiments, the enzyme that mediates a nucleic acid reaction comprises a DNA polymerase (e.g., a heat-stable DNA polymerase, such as a Taq polymerase) used in PCR or a reverse transcriptase used in PCR, or both.

Polymerase chain reaction (PCR) includes standard PCR and variations thereof, such as allele-specific PCR, assembly PCR, asymmetric PCR, dial-out PCR, hot-start PCR, intersequence-specific PCR, inverse PCR, isothermal PCR (e.g., helicase-dependent amplification and PAN-AC), ligation-mediated PCR, methylation-specific PCR, mini-primer PCR, multiplex ligation-dependent probe amplification, multiplex PCR, nested PCR, overlap-extension PCR, picotiter PCR, quantitative PCR, real-time PCR, restriction fragment length polymorphism PCR, reverse transcription PCR (RT-PCR), single-cell PCR, solid-phase PCR (e.g., standard solid-phase PCR, enhanced solid-phase PCR, bridge PCR, and polony amplification), thermal asymmetric interlaced PCR, touchdown (step-down) PCR, and universal fast walking PCR.

In further embodiments, the composition comprises a polynucleotide used in a nucleic acid reaction. In some embodiments, the polynucleotide comprises at least one primer used in PCR or reverse transcription. In certain embodiments, the at least one primer used in PCR or reverse transcription comprises at least one pair of a forward primer and a reverse primer for amplifying at least one nucleic acid (e.g., genetic) locus, or at least one reverse transcription primer for reverse transcribing at least one polyribonucleotide, or both. In some embodiments, the at least one pair of forward primer and reverse primer is labeled with a dye (e.g., a fluorescent dye) or the at least one reverse transcription primer is labeled with a dye (e.g., a fluorescent dye), or both. A reverse transcription primer refers to a polynucleotide primer used for reverse transcribing at least one polyribonucleotide to produce at least one polydeoxyribonucleotide complementary to the at least one polyribonucleotide.

In some embodiments, the composition comprises a plurality of different pairs of forward and reverse primers for amplifying a plurality of different short tandem repeat (STR) loci utilized in a forensic database, such as the Combined DNA Index System (CODIS) recommended by the Federal Bureau of Investigation (FBI). CODIS presently utilizes 13 STR loci dubbed CSF1PO, D3S1358, D5S818, D7S820, D8S1179, D13S317, D16S539, D18S51, D21S11, FGA, TH01, TPDX and vWA. In certain embodiments, the composition comprises at least 5 or at least 10, or 13, different pairs of forward and reverse primers for amplifying at least 5 or at least 10, or all 13, CODIS STR loci. In further embodiments, the composition further comprises at least one pair of forward and reverse primers for amplifying at least one other STR locus useful for human identification, such as Penta D and Penta E. In additional embodiments, the composition further comprises at least one pair of forward and reverse primers for amplifying at least one nucleic acid (e.g., genetic) locus useful for sex determination, such as amelogenin (AMEL). In certain embodiments, the composition comprises 16 different pairs of forward and reverse primers for amplifying all 13 CODIS STR loci, Penta D, Penta E and amelogenin. In some embodiments, each of the 16 different pairs of forward and reverse primers is labeled with a dye (e.g., a fluorescent dye), which may be the same as or different from the dyes used to label the other pairs of forward and reverse primers (e.g., three, four or more spectrally resolvable fluorescent dyes can be used to label the 16 different pairs of forward and reverse primers).

In additional embodiments, the composition comprises one or more reagents for performing PCR, wherein the reagents for performing PCR comprise a DNA polymerase and at least one pair of a forward primer and a reverse primer for amplifying at least one nucleic acid (e.g., genetic) locus, and the at least one pair of forward primer and reverse primer optionally is labeled with a dye (e.g., a fluorescent dye). In some embodiments, the at least one pair of forward and reverse primers comprises at least 5 or 10 different pairs of forward and reverse primers for amplifying at least 5 or 10 different STR loci utilized in a forensic database (e.g., CODIS), wherein each of the at least 5 or 10 different pairs of forward and reverse primers optionally is labeled with a dye (e.g., a fluorescent dye). In certain embodiments, the at least one pair of forward and reverse primers comprises 16 different pairs of forward and reverse primers for amplifying all 13 CODIS STR loci, Penta D, Penta E and amelogenin. In some embodiments, each of the 16 different pairs of forward and reverse primers is labeled with a dye (e.g., a fluorescent dye), which may be the same as or different from the dyes used to label the other pairs of forward and reverse primers (e.g., three, four or more spectrally resolvable fluorescent dyes can be used to label the 16 different pairs of forward and reverse primers). In certain embodiments, the DNA polymerase comprises a DNA polymerase that is stable at elevated temperature (e.g., at about 60° C., 70° C., 80° C., 90° C. or higher), such as a Taq polymerase. In further embodiments, the reagents for performing PCR further comprise deoxyribonucleotide triphosphates. In additional embodiments, the reagents for performing PCR further comprise a buffer or a metal salt (e.g., an $M^{+1}$ or $M^{+2}$ salt, such as magnesium chloride), or both.

In some embodiments, the composition comprises the DNA polymerase, the at least one pair of forward and reverse primers, deoxyribonucleotide triphosphates, and optionally a buffer and/or a metal salt (e.g., an $M^{+1}$ or $M^{+2}$ salt, such as magnesium chloride) for performing PCR. In other embodiments, the composition comprises the DNA polymerase and no primer, where the composition can further comprise deoxyribonucleotide triphosphates and optionally a buffer and/or a metal salt (e.g., an $M^{+1}$ or $M^{+2}$ salt, such as magnesium chloride). In yet other embodiments, the composition comprises the at least one pair of forward and reverse primers and no DNA polymerase, where the composition can further comprise deoxyribonucleotide triphosphates and optionally a buffer and/or a metal salt (e.g., an $M^{+1}$ or $M^{+2}$ salt, such as magnesium chloride). A kit containing reagents for performing PCR can contain, for example: a composition comprising the DNA polymerase, the at least one pair of forward and reverse primers, deoxyribonucleotide triphosphates, and optionally a buffer and/or a metal salt; or (i) a composition comprising the DNA polymerase and no primer, which can further comprise deoxyribonucleotide triphosphates and optionally a buffer and/or a metal salt; and (ii) a separate composition comprising the at least one pair of forward and reverse primers and no DNA polymerase, which can further comprise deoxyribonucleotide triphosphates and optionally a buffer and/or a metal salt.

In some embodiments, the composition comprises one or more PCR reagents for amplifying at least one nucleic acid (e.g., genetic) sequence of the DNA of a microbe or a pathogen, such as the DNA of any bacterium described herein, the DNA of any fungus described herein, and the DNA of any DNA virus described herein. A kit can contain a composition comprising all of the PCR reagents for amplifying at least one nucleic acid (e.g., genetic) sequence of the DNA of a microbe or a pathogen, or two or more compositions that in total comprise all of the PCR reagents.

In other embodiments, the composition comprises one or more reagents for performing reverse transcription, wherein the reagents for performing reverse transcription comprise a reverse transcriptase and at least one reverse transcription primer for reverse transcribing at least one polyribonucleotide, and the at least one reverse transcription primer optionally is labeled with a dye (e.g., a fluorescent dye). In further embodiments, the reagents for performing reverse transcription further comprise deoxyribonucleotide triphosphates. In additional embodiments, the reagents for performing reverse transcription further comprise a buffer or a metal salt (e.g., an $M^{+1}$ or $M^{+2}$ salt, such as magnesium chloride), or both.

In some embodiments, the composition comprises the reverse transcriptase, the at least one reverse transcription primer, deoxyribonucleotide triphosphates and optionally a buffer and/or a metal salt (e.g., an $M^{+1}$ or $M^{+2}$ salt, such as magnesium chloride) for performing reverse transcription. In other embodiments, the composition comprises the reverse transcriptase and no reverse transcription primer, where the composition can further comprise deoxyribonucleotide triphosphates and optionally a buffer and/or a metal salt (e.g., an $M^{+1}$ or $M^{+2}$ salt, such as magnesium chloride). In yet other embodiments, the composition comprises the at least one reverse transcription primer and no reverse transcriptase, where the composition can further comprise deoxyribonucleotide triphosphates and optionally a buffer and/or a metal salt (e.g., an $M^{+1}$ or $M^{+2}$ salt, such as magnesium chloride). A kit containing reagents for performing reverse transcription can contain, for example: a composition comprising the reverse transcriptase, the at least one reverse transcription primer, deoxyribonucleotide triphosphates and optionally a buffer and/or a metal salt; or (i) a composition comprising the reverse transcriptase and no reverse transcription primer, which can further comprise deoxyribonucleotide triphosphates and optionally a buffer and/or a metal salt; and (ii) a separate composition comprising the at least one reverse transcription primer and no reverse transcriptase, which can further comprise deoxyribonucleotide triphosphates and optionally a buffer and/or a metal salt.

In further embodiments, the composition may comprise one or more reagents for performing reverse transcription PCR (RT-PCR), wherein the reagents for performing RT-PCR comprise a reverse transcriptase, a DNA polymerase, at least one reverse transcription primer for reverse transcribing at least one polyribonucleotide to produce at least one polydeoxyribonucleotide complementary to the at least one polyribonucleotide, and at least one pair of a forward primer and a reverse primer for amplifying the at least one complementary polydeoxyribonucleotide; and the at least one reverse transcription primer optionally is labeled with a dye (e.g., a fluorescent dye) and the at least one pair of forward primer and reverse primer optionally is labeled with a dye (e.g., a fluorescent dye).

In certain embodiments, the DNA polymerase comprises a DNA polymerase that is stable at elevated temperature (e.g., at about 60° C., 70° C., 80° C., 90° C. or higher), such as a Taq polymerase. In additional embodiments, the reagents for performing RT-PCR further comprise deoxyribonucleotide triphosphates. In certain embodiments, the reagents for performing RT-PCR further comprise a buffer or a metal salt (e.g., an $M^{+1}$ or $M^{+2}$ salt, such as magnesium chloride), or both.

In some embodiments, the composition comprises the reverse transcriptase, the DNA polymerase, the at least one reverse transcription primer, the at least one pair of forward and reverse primers, deoxyribonucleotide triphosphates, and optionally a buffer and/or a metal salt (e.g., an $M^{+1}$ or $M^{+2}$ salt, such as magnesium chloride) for performing RT-PCR. In other embodiments, the composition comprises the reverse transcriptase, the DNA polymerase, no reverse transcription primer, and no pair of forward and reverse primers, where the composition can further comprise deoxyribonucleotide triphosphates and optionally a buffer and/or a metal salt (e.g., an $M^{+1}$ or $M^{+2}$ salt, such as magnesium chloride). In yet other embodiments, the composition comprises the at least one reverse transcription primer, the at least one pair of forward and reverse primers, no reverse transcriptase, and no DNA polymerase, where the composition can further comprise deoxyribonucleotide triphosphates and optionally a buffer and/or a metal salt (e.g., an $M^{+1}$ or $M^{+2}$ salt, such as magnesium chloride). A kit containing reagents for performing RT-PCR can contain, for example: a composition comprising the reverse transcriptase, the DNA polymerase, the at least one reverse transcription primer, the at least one pair of forward and reverse primers, deoxyribonucleotide triphosphates, and optionally a buffer and/or a metal salt; or (i) a composition comprising the reverse transcriptase, the DNA polymerase, no reverse transcription primer, and no pair of forward and reverse primers, which can further comprise deoxyribonucleotide triphosphates and optionally a buffer and/or a metal salt; and (ii) a separate composition comprising the at least one reverse transcription primer, the at least one pair of forward and reverse primers, no reverse transcriptase, and no DNA polymerase, which can further comprise deoxyribonucleotide triphosphates and optionally a buffer and/or a metal salt.

In some embodiments, the composition comprises one or more RT-PCR reagents for amplifying at least one polydeoxyribonucleotide complementary to at least one nucleic acid (e.g., genetic) sequence of the RNA of an RNA virus, such as the RNA of any RNA virus described herein. A kit can contain a composition comprising all of the RT-PCR reagents for amplifying at least one polydeoxyribonucleotide complementary to at least one nucleic acid (e.g., genetic) sequence of the RNA of an RNA virus, or two or more compositions that in total comprise all of the RT-PCR reagents.

In additional embodiments, the composition comprises reagents for performing transcription, wherein the reagents for performing transcription comprise an RNA polymerase. In further embodiments, the reagents for performing transcription further comprise ribonucleotide triphosphates. In certain embodiments, the reagents for performing transcription further comprise a buffer or a metal salt (e.g., an $M^{+1}$ or $M^{+2}$ salt, such as magnesium chloride), or both.

In further embodiments, the composition comprises a polypeptide that regulates (e.g., agonizes or antagonizes/inhibits) an enzyme. Non-limiting examples of polypeptides that regulate enzymes include polypeptides that inhibit proteases, such as the protease inhibitors described herein.

In other embodiments, the composition comprises an antibody. In some embodiments, the antibody is used in an immunoassay. In certain embodiments, the immunoassay is an enzyme-linked immunosorbent assay (ELISA) or a sandwich immunoassay. In further embodiments, the antibody used in an immunoassay comprises an unlinked antibody, an antibody bound to a solid substrate (e.g., a bead), an antibody conjugated to a detection protein or enzyme or a fragment thereof, or any combination thereof, wherein the antibody may or may not be labeled with a dye (e.g., a fluorescent dye, a chemiluminescent dye, or a phosphorescent dye).

In some embodiments, the composition comprises one or more reagents for performing an immunoassay, wherein the one or more reagents for performing an immunoassay comprise an antibody that has affinity for or is specific for a target antigen or analyte, the antibody is labeled with a dye (e.g., a fluorescent dye, a chemiluminescent dye, or a phosphorescent dye) or is conjugated to a detection protein or enzyme or a fragment thereof, and the antibody optionally is bound to a solid substrate (e.g., a bead).

In further embodiments, the composition comprises one or more reagents for performing a sandwich immunoassay, wherein: the reagents for performing a sandwich immunoassay comprise a first antibody that has affinity for or is specific for a target antigen or analyte and a second antibody that has affinity for or is specific for the target antigen or analyte; the second antibody is labeled with a dye (e.g., a fluorescent dye, a chemiluminescent dye, or a phosphorescent dye) or is conjugated to a detection protein or enzyme or a fragment thereof; and the first antibody optionally is bound to a solid substrate (e.g., a bead).

In some embodiments, the composition comprises the first antibody and the second antibody. In other embodiments, the composition comprises the first antibody and not the second antibody. In yet other embodiments, the composition comprises the second antibody and not the first antibody. A kit containing reagents for performing a sandwich immunoassay can contain, for example: a composition comprising the first antibody and the second antibody; or (i) a composition comprising the first antibody and not the second antibody; and (ii) a separate composition comprising the second antibody and not the first antibody.

In additional embodiments, the composition comprises one or more reagents for performing an enzyme-linked immunosorbent assay (ELISA), wherein the reagents for performing ELISA comprise: a detection antibody that has affinity for or is specific for a target antigen or analyte and is conjugated to a detection enzyme or a fragment thereof; or a first antibody that has affinity for or is specific for a target antigen or analyte, and a second antibody that has affinity for or is specific for the first antibody and is conjugated to a detection enzyme or a fragment thereof.

In some embodiments, the composition comprises the detection antibody. In other embodiments, the composition comprises the first antibody and the second antibody. In yet other embodiments, the composition comprises the first antibody and not the second antibody. In still other embodiments, the composition comprises the second antibody and not the first antibody. A kit containing reagents for performing an ELISA can contain, for example: a composition comprising the detection antibody; or a composition comprising the first antibody and the second antibody; or (i) a composition comprising the first antibody and not the second antibody; and (ii) a separate composition comprising the second antibody and not the first antibody.

The detection protein or enzyme or a fragment thereof that is conjugated to an antibody used in an immunoassay can be any protein or enzyme or any fragment thereof that is suitable for detection. In certain embodiments, the detection protein or enzyme or a fragment thereof that is conjugated to an antibody used in an immunoassay is selected from the group consisting of: phycobiliproteins, phycoerythrins, B-phycoerythrin, R-phycoerythrin, and fragments and conjugates thereof; streptavidin, avidin, deglycosylated avidin, and fragments and conjugates thereof; peroxidases, horseradish peroxidase, and fragments and conjugates thereof; and phosphatases, alkaline phosphatase, and fragments and conjugates thereof.

In further embodiments, the composition comprises a protein or enzyme useful for detection, where the protein or enzyme may or may not be conjugated to an antibody. Non-limiting examples of proteins and enzymes useful for detection include: phycobiliproteins, phycoerythrins, B-phycoerythrin, R-phycoerythrin, and conjugates thereof (e.g., phycoerythrin-streptavidin conjugates, phycoerythrin-alkaline phosphatase conjugates, and phycoerythrin-antibody conjugates); streptavidin, avidin, deglycosylated avidin, and conjugates thereof (e.g., streptavidin-horse radish peroxidase conjugates and streptavidin-antibody conjugates); peroxidases, horseradish peroxidase, and conjugates thereof (e.g., horseradish peroxidase-antibody conjugates); and phosphatases, alkaline phosphatase, and conjugates thereof (e.g., alkaline phosphatase-antibody conjugates).

In additional embodiments, the composition comprises a polypeptide aptamer that binds specifically to a target ligand (e.g., a small molecule, a protein, a nucleic acid, a cell, a tissue or an organism). In some embodiments, the polypeptide aptamer comprises a variable peptide domain or loop (e.g., a domain or loop containing about 10 to about 20 amino acids) attached at both ends to a polypeptide scaffold (e.g., a protein scaffold, such as thioredoxin A).

The composition can also contain other kinds of polypeptides, including without limitation receptors (e.g., peripheral membrane proteins, transmembrane proteins and nuclear receptors), polypeptide ligands (e.g., polypeptide ligands of antibodies), regulatory factors, hormones, cytokines (e.g., interferons and interleukins), structural proteins (e.g., collagen and elastin), and toxins. Non-limiting examples of hormones include adrenocorticotropic hormone, angiotensin II, antidiuretic hormone (vasopressin), basic fibroblast growth factor-2, cholecystokinin, colony-stimulating factors (e.g., granulocyte colony-stimulating factor), gastrin, growth hormone, insulin, leptin, atrial natriuretic peptide, brain natriuretic peptide, C-type natriuretic peptide, oxytocin, parathyroid hormone-related protein, prolactin, and somatostatin. Examples of toxins include without limitation cyanotoxins, cytotoxins, exotoxins (e.g., botulinum toxin and *Corynebacterium diphtheriae* exotoxin), hemotoxins, hepatotoxins (e.g., amatoxins and phallotoxins), mycotoxins, necrotoxins, neurotoxins (e.g., bungarotoxins, chlorotoxin, conotoxins and tetanus toxin), plant toxins (e.g., ricin), insect toxins (e.g., apitoxin), and snake toxins [e.g., cardiotoxins, myotoxins, neurotoxins (such as alpha-neurotoxins, beta-neurotoxins and dendrotoxins), sarafotoxins, hydrolases (such as phosphodiesterases and phospholipases), lyases, oxydoreductases (such as L-amino acid oxidases), transferases, hemorrhagins, hyaluronidases, thrombin-like pro-coagulants, and kallikrein-like serine proteases].

Furthermore, the composition can preserve polypeptide therapeutics (e.g., hormone therapeutics, cytokine therapeutics, antibody therapeutics, fusion protein therapeutics, antithrombotics, and toxin therapeutics) and vaccines in a substantially water-free fluid medium, e.g., without the need for refrigeration. Hormone therapeutics include without limitation erythropoietin, growth hormone, insulin, and other hormones described herein. Cytokine therapeutics include without limitation interferons [e.g., interferon alpha (including interferon alpha-2a and interferon alpha-2b), interferon beta (including interferon beta-1a and interferon beta-1b), and derivatives thereof (including interferons derivatived with polyethylene glycol (PEG))] and interleukins (e.g., interleukin 2 and interleukin 12). Non-limiting examples of antibody therapeutics include adalimumab, bevacizumab, infliximab, trastuzumab, and ustekinumab. Fusion protein therapeutics include without limitation abatacept, alefacept, denileukin diftitox, and etanercept.

Non-limiting examples of antithrombotics include antiplatelet agents (e.g., abciximab), anticoagulants (e.g., antithrombin, batroxobin, hementin, hirudin, lepirudin and bivalirudin), and thrombolytics [e.g., tissue plasminogen activators (including alteplase, reteplase and tenecteplase), anistreplase, streptokinase and urokinase]. Examples of toxin therapeutics include without limitation botulinum toxin, chlorotoxin, and toxoids used as vaccines (e.g., against botulism, diphtheria and tetanus). Non-limiting examples of vaccines include vaccines against botulism, bubonic plague, chicken pox, cholera, diphtheria, hepatitis, influenza, measles, mumps, polio, rabies, rubella, small pox, tetanus, tuberculosis, typhoid, and yellow fever.

In some embodiments, the composition contains a pharmaceutical formulation comprising a polypeptide and optionally one or more other substances as described herein. In certain embodiments, the concentration of the polypeptide in the composition is at least about 10 mg/mL, 50 mg/mL, 100 mg/mL, 200 mg/mL, 300 mg/mL, 400 mg/mL, 500 mg/mL or 1 g/mL, or about 100-1000 mg/mL, 100-500 mg/mL or 500-1000 mg/mL. In some embodiments, the concentration of the polypeptide in the composition is at least about 100 mg/mL, or about 100-1000 mg/mL.

In further embodiments, the composition comprises a catalytic polynucleotide. In some embodiments, the catalytic polynucleotide is a natural or synthetic ribozyme (or RNA enzyme or catalytic RNA). Non-limiting examples of natural ribozymes include peptidyl transferase 23S rRNA, RNase P, Group I introns, Group II introns, GIR1 branching ribozyme, leadzyme, hairpin ribozyme, hammerhead ribozyme, HDV ribozyme, mammalian CPEB3 ribozyme, VS ribozyme, glmS ribozyme, and CoTC ribozyme. Examples of synthetic ribozymes include without limitation ribozymes produced from RNA polymerases (e.g., Round 18 RNA polymerase ribozyme and variants thereof, such as B6.61 ribozyme and tC19Z ribozyme) and ribozymes produced from RNA ligases. In other embodiments, the catalytic polynucleotide is a deoxyribozyme (or DNA enzyme or catalytic DNA), including deoxyribozymes that catalyze DNA phosphorylation, DNA adenylation, DNA deglycosylation, DNA cleavage, thymine dimer photoreversion, and porphyrin metalation.

In additional embodiments, the composition comprises a polynucleotide that binds specifically to a target ligand (e.g., a small molecule, a protein, a nucleic acid, a cell, a tissue or an organism). In some embodiments, the polynucleotide that binds specifically to a target ligand is a natural or synthetic nucleic acid aptamer (e.g., DNA aptamer, RNA aptamer or XNA aptamer).

Non-limiting examples of nucleic acid aptamers include DNA aptamers and RNA aptamers that bind dopamine, hemin, HIV trans-acting responsive element, interferons (e.g., interferon-gamma), lysozymes, mycotoxins, thrombin, and vascular endothelial growth factor (VEGF).

In other embodiments, the composition comprises a biological sample. The biological sample can be, e.g., a clinical sample, a surgical sample, a laboratory sample, a research sample, a forensic sample, a veterinary sample, an environmental sample, an agricultural sample, or an industrial sample. The biological sample can be re-hydrated by addition of water or an aqueous solution (e.g., an aqueous buffer) for analysis, if desired. In some embodiments, the biological sample comprises whole or fractionated animal (e.g., mammalian, such as human) blood. In further embodiments, the biological sample comprises whole or fractionated animal (e.g., mammalian, such as human) plasma. In still further embodiments, the biological sample comprises whole or fractionated animal (e.g., mammalian, such as human) serum.

In additional embodiments, the biological sample comprises cells. A cell can be, e.g., a eukaryotic or prokaryotic cell from any single-celled or multi-celled organism, and can be of any type. In some embodiments, the biological sample comprises animal cells, mammalian cells, human cells, plant cells, microbial cells, pathogenic cells, bacterial cells, fungal cells, protozoan cells or viral particles, or any combination thereof, or lysates or extracts thereof. The cells or viral particles can be dissolved or suspended in a natural fluid or a laboratory culture medium (e.g., Dulbecco's phosphate buffered saline with 2% fetal bovine serum, Eagle's minimum essential medium (EMEM), Dulbecco's modified Eagle's medium (DMEM), or the allantoic fluid of embryonated chicken eggs) and then transferred to the substantially water-free fluid medium containing the at least one alcohol solvent (or the at least one ionic organic solvent in other embodiments of a composition comprising a biological material in a substantially water-free fluid medium, as described below).

In some embodiments, the biological sample comprises a bacterium. The bacterium can be non-pathogenic or pathogenic. Non-limiting examples of bacteria include *Bacillus* (e.g., *Bacillus anthracis, Bacillus cereus* and *Bacillus thuringiensis*); *Bordetella* (e.g., *Bordetella pertussis*); *Borrelia* (e.g., *Borrelia burgdorferi*); *Brucella* (e.g., *Brucella abortus, Brucella canis, Brucella melitensis*, and *Brucella suis*); *Campylobacter* (e.g., *Campylobacter jejuni*); *Chlamydia* and *Chlamydophila* (e.g., *Chlamydia pneumoniae, Chlamydia trachomatis*, and *Chlamydophila psittaci*); *Clostridium* (e.g., *Clostridium botulinum, Clostridium difficile, Clostridium perfringens*, and *Clostridium tetani*); *Corynebacterium* (e.g., *Corynebacterium diphtheriae*); *Enterococcus* (e.g., *Enterococcus faecalis* and *Enterococcus faecium*); *Escherichia* (e.g., *Escherichia coli*); *Francisella* (e.g., *Francisella tularensis*); *Haemophilus* (e.g., *Haemophilus influenzae*); *Helicobacter* (e.g., *Helicobacter pylori*); *Legionella* (e.g., *Legionella pneumophila*); *Leptospira* (e.g., *Leptospira interrogans*); *Listeria* (e.g., *Listeria monocytogenes*); *Mycobacterium* (e.g., *Mycobacterium leprae, Mycobacterium tuberculosis*, and *Mycobacterium ulcerans*); *Mycoplasma* (e.g., *Mycoplasma pneumoniae*); *Neisseria* (e.g., *Neisseria gonorrhoeae* and *Neisseria meningitidis*); *Pseudomonas* (e.g., *Pseudomonas aeruginosa*); *Rickettsia* (e.g., *Rickettsia rickettsii*); *Salmonella* (e.g., *Salmonella typhi* and *Salmonella typhimurium*); *Shigella* (e.g., *Shigella sonnei*); *Staphylococcus* (e.g., *Staphylococcus aureus, Staphylococcus epidermidis*, and *Staphylococcus saprophyticus*); *Streptococcus* (e.g., *Streptococcus agalactiae, Streptococcus pneumoniae*, and *Streptococcus pyogenes*); *Treponema* (e.g., *Treponema pallidum*); *Vibrio* (e.g., *Vibrio cholerae* and *Vibrio parahaemolyticus*); and *Yersinia* (e.g., *Yersinia pestis*).

In other embodiments, the biological sample comprises a fungus. The fungus can be non-pathogenic or pathogenic. Examples of fungi include without limitation *Aspergillus* (e.g., *Aspergillus clavatus, Aspergillus fumigatus*, and *Aspergillus flavus*); *Blastomyces* (e.g., *Blastomyces dermatitidis*); *Candida* (e.g., *Candida albicans*); *Coccidioides* (e.g., *Coccidioides immitis* and *Coccidioides posadasii*); *Cryptococcus* (e.g., *Cryptococcus albidus, Cryptococcus gattii, Cryptococcus laurentii*, and *Cryptococcus neoformans*); *Fusarium* (e.g., *Fusarium graminearum, Fusarium oxysporum, Fusarium proliferatum, Fusarium solani* complex, and *Fusarium verticillioides*); *Histoplasma* (e.g., *Histoplasma capsulatum*); *Pneumocystis* [e.g., *Pneumocystis jirovecii* (or *Pneumocystis carinii*)]; *Stachybotrys* (e.g., *Stachybotrys chartarum*); *Trichosporon* (e.g., *Trichosporon asahii, Trichosporon asteroides, Trichosporon cutaneum, Trichosporon dermatis, Trichosporon dohaense, Trichosporon inkin, Trichosporon loubieri, Trichosporon mucoides* and *Trichosporon ovoides*); and Zygomycetes (e.g., *Rhizopus stolonifer*).

In yet other embodiments, the biological sample comprises a protozoan. The protozoan can be non-pathogenic or pathogenic. Examples of protozoa include without limitation *Balantidium* (e.g., *Balantidium coli*); *Cryptosporidium* (e.g., *Cryptosporidium canis, Cryptosporidium fells, Cryptosporidium hominis, Cryptosporidium meleagridis, Cryptosporidium muris* and *Cryptosporidium parvum*); *Entamoeba* (e.g., *Entamoeba dispar* and *Entamoeba histolytica*); *Giardia* (e.g., *Giardia lamblia* and *Giardia muris*); *Leishmania* (e.g., *Leishmania braziliensis, Leishmania infantum* and *Leishmania major*); *Naegleria* (e.g., *Naegleria fowleri*); *Plasmodia* (e.g., *Plasmodia falciparum, Plasmodia knowlesi, Plasmodia malariae* and *Plasmodia vivax*); *Toxoplasma* (e.g., *Toxoplasma gondii*); *Trichomonas* (e.g., *Trichomonas vaginalis*); and *Trypanosoma* (e.g., *Trypanosoma brucei* and *Trypanosoma cruzi*).

In additional embodiments, the biological sample comprises a virus. The virus can be a DNA virus or an RNA virus. Non-limiting examples of DNA viruses include adenoviruses [including Atadenovirus (e.g., ovine adenovirus D), Aviadenovirus (e.g., fowl adenovirus A), Ichtadenovirus (e.g., sturgeon adenovirus A), Mastadenovirus (e.g., human adenovirus C and AD-36), and Siadenovirus (e.g., frog adenovirus)]; hepadnaviruses [including Orthohepadnavirus (e.g., hepatitis B virus) and Avihepadnavirus (e.g., duck hepatitis B virus)]; herpesviruses [including human herpesviruses (e.g., herpes simplex virus-1, herpes simplex virus-2, Varicella zoster virus, Epstein-Barr virus, cytomegalovirus, roseolovirus, herpes lymphotropic virus, pityriasis rosea virus, and Kaposi's sarcoma-associated herpesvirus) and zoonotic herpesviruses (e.g., cercopithecine herpesvirus-1 and murine gammaherpesvirus-68)]; papillomaviruses (e.g., human papillomaviruses 1 to 18); and polyomaviruses [including Orthopolyomavirus (e.g., simian virus 40, B-lymphotropic polyomavirus, baboon polyomavirus 1, bat polyomavirus, BK polyomavirus, Bornean orang-utan polyomavirus, Sumatran orang-utan polyomavirus, bovine polyomavirus, California sea lion polyomavirus, chimpanzee polyomavirus, hamster polyomavirus, JC polyomavirus, Merkel cell polyomavirus, murine pneumotropic virus, murine polyomavirus, squirrel monkey polyomavirus, and trichodysplasia spinuolsa-associated polyomavirus), Wukipolyomavirus (e.g., human polyomaviruses 6 and 7, KI polyomavirus, and WU polyomavirus), Avipolyomavirus (e.g., avian polyomavirus, canary polyomavirus, crow polyomavirus, finch polyomavirus, and goose hemorrhagic polyomavirus), and human polyomavirus 9].

Non-limiting examples of RNA viruses include coronaviruses [including human coronaviruses (e.g., SARS coronavirus)]; flaviviruses [including Flavivirus (e.g., yellow fever virus, West Nile virus, and dengue fever virus), Hepacivirus (e.g., hepatitis C virus), Hepatitis G Virus (e.g., the GB agent and hepatitis G virus), and Pestivirus (e.g., bovine viral diarrhea virus, classical swine fever virus, and hog cholera virus)]; orthomyxoviruses [including Influenzavirus A (e.g., influenza A virus), Influenzavirus B (e.g., influenza B virus), Influenzavirus C (e.g., influenza C virus), Isavirus (e.g., infectious salmon anemia virus), and Thogotovirus (e.g., Dhori virus and Thogoto virus)]; paramyxoviruses [including Aquaparamyxovirus (e.g., Atlantic salmon paramyxovirus and Pacific salmon paramyxovirus), Avulavirus (e.g., Newcastle disease virus), Ferlavirus (e.g., Fer-de-Lance virus), Henipavirus (e.g., hendravirus and nipahvirus), Morbillivirus (e.g., measles virus, canine distemper virus, ovine rinderpest virus, phocine distemper virus, and rinderpest virus), Respirovirus (e.g., human parainfluenza viruses 1 and 3, and Sendai virus), Rubulavirus (e.g., mumps virus, human parainfluenza viruses 2 and 4, Menangle virus, simian parainfluenza virus 5, Tioman virus, and Tuhokoviruses 1, 2 and 3), TPMV-like viruses (e.g., Mossman virus, Nariva virus, Salem virus, and Tupaia paramyxovirus), Beilong virus, Pneumovirus (e.g., human respiratory syncytial virus and bovine respiratory syncytial virus), Metapneumovirus (e.g., human metapneumovirus and avian pneumovirus), J virus, Sunshine virus, and Tailam virus]; picornaviruses [including Aphthovirus (e.g., foot-and-mouth disease virus, bovine rhinitis A virus, bovine rhinitis B virus, and equine rhinitis A virus), Avihepatovirus (e.g., duck hepatitis A virus), Cardiovirus (e.g., encephalomyocarditis virus and Theilovirus), Enterovirus (e.g., human enteroviruses A to D, simian enterovirus A, bovine enterovirus, porcine enterovirus B, and human rhinoviruses A to C), Erbovirus (e.g., equine rhinitis B virus), Hepatovirus (e.g., hepatitis A virus), Kobuvirus (e.g., Aichi virus and bovine kobuvirus), Parechovirus (e.g., human parechovirus and Ljungan virus), Salivirus (e.g., Salivirus A), Sapelovirus (e.g., avian sapelovirus, porcine sapelovirus, and simian sapelovirus), Senecavirus (e.g., Seneca Valley virus), Teschovirus (e.g., porcine teschovirus), and Tremovirus (e.g., avian encephalomyelitis virus)]; retroviruses [including Alpharetrovirus (e.g., avian leukosis virus and rous sarcoma virus), Betaretrovirus (e.g., mouse mammary tumour virus), Gammaretrovirus (e.g., murine leukemia virus and feline leukemia virus), Deltaretrovirus (e.g., human T-lymphotropic virus and bovine leukemia virus), Epsilonretrovirus (e.g., Walleye dermal sarcoma virus), Lentivirus (e.g., human immunodeficiency viruses (HIV), simian immunodeficiency viruses, and feline immunodeficiency viruses), and Spumavirus (e.g., simian foamy virus)]; rhabdoviruses [including Cytorhabdovirus (e.g., lettuce necrotic yellows virus), Dichorhabdovirus (e.g., orchid fleck virus), Ephemerovirus (e.g., bovine ephemeral fever virus), Lyssavirus (e.g., rabies virus), Novirhabdovirus (e.g., infectious hematopoietic necrosis virus), Nucleorhabdovirus (e.g., potato yellow dwarf virus), and Vesiculovirus (e.g., vesicular stomatitis Indiana virus)]; and togaviruses [including Rubivirus (e.g., rubella virus) and Alphavirus (e.g., Chikungunya virus, Eastern equine encephalitis virus, Western equine encephalitis virus, Venezuelan equine encephalitis virus, O'nyong'nyong virus, Ross River virus, Semliki Forest virus, and Sindbis virus)].

In some embodiments, the composition containing the biological material further comprises one or more substances selected from the group consisting of reducing agents, antioxidants, free radical scavengers, oxygen radical scavengers, hydroxyl radical scavengers, singlet oxygen quenchers, hydroperoxide-removing agents, protease inhibitors, nuclease inhibitors, ribonuclease (RNase) inhibitors, deoxyribonuclease (DNase) inhibitors, metal chelators, preservatives, anti-microbials, buffers (or buffering agents), detergents, and chaotropes. The composition can comprise the one or more substances in appropriate amounts to enhance, e.g., the stability and/or the solubility of the biological material in the substantially water-free fluid medium. It is understood that a substance can have one or more functions or properties. As an example, a substance can be a reducing agent, an antioxidant, a free radical scavenger, an oxygen radical scavenger, a hydroxyl radical scavenger or a singlet oxygen quencher, or any combination thereof. As another example, a substance can be a metal chelator, a DNase inhibitor or an anti-microbial, or any combination thereof.

Examples of reducing agents, antioxidants, and free radical scavengers include without limitation cysteine, dithionite, dithioerythritol, dithiothreitol (DTT), dyseine, 2-mercaptoethanol, mercaptoethylene, bisulfite, sodium metabisulfite, pyrosulfite, pentaerythritol, thioglycolic acid, urea, uric acid, vitamin C, vitamin E, superoxide dismutases, and analogs, derivatives and salts thereof.

Non-limiting examples of oxygen radical scavengers include sugar alcohols (e.g., erythritol, mannitol, sorbitol, and xylitol), monosaccharides (e.g., hexoses, allose, altrose, fructose, fucose, fuculose, galactose, glucose, gulose, idose, mannose, rhamnose, sorbose, tagatose, talose, pentoses, arabinose, lyxose, ribose, deoxyribose, ribulose, xylose, xylulose, tetroses, erythrose, erythrulose, and threose), disaccharides (e.g., cellobiose, lactose, maltose, sucrose, and trehalose), complex sugars (e.g., trisaccharides, kestose, isomaltotriose, maltotriose, maltotriulose, melezitose, nigerotriose, raffinose, tetrasaccharides, stachyose, fructo-polysaccharides, galacto-polysaccharides, mannan-polysaccharides, gluco-polysaccharides, glycogen, starch, amylose, amylopectin, dextrin, cellulose, glucans, beta-glucans, dextran, fructans, inulin, glucosamine polysaccharides, chitin, aminoglycosides, apramycin, gentamycin, kanamycin, netilmicin, neomycin, paromomycin, streptomycin, tobramycin, glycosaminoglycans (mucopolysaccharides), chondroitin sulfate, dermatan sulfate, keratan sulfate, heparin, heparan sulfate, and hyaluronan), and analogs, derivatives and salts thereof.

Examples of hydroxyl radical scavengers include without limitation azides (e.g., sodium azide), cysteine, dimethylsulfoxide, histidine, salicylic acid, salicylate, sugar alcohols (e.g., erythritol, mannitol, sorbitol, and xylitol), monosaccharides (e.g., those described herein), disaccharides (e.g., cellobiose, lactose, maltose, sucrose, and trehalose), complex sugars (e.g., those described herein), and analogs, derivatives and salts thereof.

Non-limiting examples of singlet oxygen quenchers include azides (e.g., sodium azide), ascorbic acid, ascorbate, alkyl imidazoles (e.g., carnosine, histamine, histidine, and imidazole 4-acetic acid), indoles (e.g., tryptophan and derivatives thereof, such as N-acetyl-5-methoxytryptamine, N-acetyl serotonin, and 6-methoxy-1,2,3,4-tetrahydro-beta-carboline), sulfur-containing amino acids (e.g., cysteine, S-allyl-cysteine, S-aminoethyl-cysteine, djenkolic acid, ethionine, methionine, N-formyl-methionine, lanthionine, and felinine), phenolic compounds (e.g., tyrosine and derivatives thereof), aromatic carboxylic acids (e.g., salicylic acid and derivatives thereof), vitamin A and derivatives thereof (e.g., carotenoids, beta-carotene, retinol and retinal), vitamin E and derivatives thereof (e.g., tocopherols, alpha-tocopherol and tocotrienols), and analogs, derivatives and salts thereof.

Examples of hydroperoxide-removing agents include without limitation catalase, glutathione, peroxidases, glutathione peroxidases, pyruvate, and analogs, derivatives and salts thereof.

Non-limiting examples of protease inhibitors include aspartic protease inhibitors, cysteine protease inhibitors, metalloprotease inhibitors, serine protease inhibitors, threonine protease inhibitors, trypsin inhibitors (e.g., avian egg white trypsin inhibitors, bovine trypsin inhibitors, lima bean trypsin inhibitors, and soybean trypsin inhibitors such as Kunitz trypsin inhibitor and Bowman-Birk inhibitor), Kunitz-type protease inhibitors, 4-(2-aminoethyl)benzenesulfonyl fluoride (AEBSF) and salts thereof (e.g., HCl salt), amastatin, antithrombin III, antipain, APMSF, aprotinin, bestatin, benzamidine, calpain inhibitors I and II, chymostatin, 3,4-dichloroisocoumarin, diisopropyl fluorophosphate (DFP), E-64, elastatinal, hirustasin, leupeptin, alpha-2-macroglobulin, Pefabloc SC, pepstatin, 1,10-phenanthroline, phosphoramidon, phenylmethylsulfonyl fluoride (PMSF), PMSF Plus, tissue inhibitors of metalloproteinases (e.g., TIMP-1, TIMP-2, TIMP-3 and TIMP-4), tosyllysine chloromethyl ketone (TLCK) and salts thereof (e.g., HCl salt), tosyl phenylalanyl chloromethyl ketone (TPCK), and analogs, derivatives and salts thereof.

Non-limiting examples of RNase inhibitors include mammalian ribonuclease inhibitor proteins [e.g., porcine ribonuclease inhibitor and human ribonuclease inhibitor (e.g., human placenta ribonuclease inhibitor and recombinant human ribonuclease inhibitor)], aurintricarboxylic acid (ATA) and salts thereof [e.g., triammonium aurintricarboxylate (aluminon)], adenosine 5'-pyrophosphate, 2'-cytidine monophosphate free acid (2'-CMP), 5'-diphosphoadenosine 3'-phosphate (ppA-3'-p), 5'-diphosphoadenosine 2'-phosphate (ppA-2'-p), leucine, oligovinysulfonic acid, poly(aspartic acid), tyrosine-glutamic acid polymer, 5'-phospho-2'-deoxyuridine 3'-pyrophosphate P'→5'-ester with adenosine 3'-phosphate (pdUppAp), and analogs, derivatives and salts thereof.

Examples of DNase inhibitors and metal chelators include without limitation aurintricarboxylic acid (ATA) and salts thereof [e.g., triammonium aurintricarboxylate (aluminon)], boric acid, borate, citric acid, citrate, salicylic acid, salicylate, 1,2-bis(o-aminophenoxy)ethane-N,N,N',N'-tetraacetic acid (BAPTA), diethylene triamine pentaacetic acid (DTPA), ethylenediaminetetraacetic acid (EDTA), ethylene glycol tetraacetic acid (EGTA), glycoletherdiaminetetraacetic acid (GEDTA), N-(2-hydroxyethyl)ethylenediamine-N,N',N'-triacetic acid (HEDTA), nitrilotriacetic acid (NTA), 2,2'-bipyridine, o-phenanthroline, triethanolamine, and analogs, derivatives and salts thereof.

Examples of preservatives include without limitation azides (e.g., sodium azide), polyethylene glycol (PEG), and anti-microbials (e.g., anti-biotic, anti-fungal, anti-parasitic and anti-viral agents). Anti-microbials include without limitation beta-lactams, penicillins, semi-synthetic penicillins, mono-bactams, carboxypenems, aminoglycosides, glycopeptides, lincomycins, macrolides, allylamines, azoles, polyenes, tetraenes, sulfonamides, pyrimidines, thiocarbamates, benzoic acid compounds, rifamycins, tetracyclines, reverse transcriptase inhibitors, protease inhibitors, thymidine kinase inhibitors, glycoprotein synthesis inhibitors, sugar synthesis inhibitors, glucan synthesis inhibitors, structural protein synthesis inhibitors, viral maturation inhibitors, nucleoside analogs, polypeptides, and analogs, derivatives and salts thereof. For example, anti-microbials include without limitation penicillin, cephalosporin, ampicillin, amoxycillin, aztreonam, clavulanic acid, imipenem, streptomycin, gentamycin, vancomycin, clindamycin, polymyxin, erythromycin, bacitracin, amphotericin, nystatin, rifampicin, tetracycline, chlortetracycline, doxycycline, chloramphenicol, ammolfine, butenafine, naftifine, terbinafine, ketoconazole, fluconazole, elubiol, econazole, econaxole, itraconazole, isoconazole, imidazole, miconazole, sulconazole, clotrimazole, enilconazole, oxiconazole, tioconazole, terconazole, butoconazole, thiabendazole, voriconazole, saperconazole, sertaconazole, fenticonazole, posaconazole, bifonazole, flutrimazole, nystatin, pimaricin, amphotericin B, flucytosine, natamycin, tolnaftate, mafenide, dapsone, caspofungin, actofunicone, griseofulvin, potassium iodide, Gentian Violet, ciclopirox, ciclopirox olamine, haloprogin, silver sulfadiazine, undecylenate, undecylenic acid, undecylenic alkanolamide, Carbol-Fuchsin, nevirapine, delavirdine, efavirenz, saquinavir, ritonavir, indinavir, nelfinavir, amprenavir, zidovudine (AZT), stavudine (d4T), lamivudine (3TC), didanosine (DDI), zalcitabine (ddC), abacavir, acyclovir, penciclovir, valacyclovir, ganciclovir, and analogs, derivatives and salts thereof.

In some embodiments, the buffers or buffering agents provide buffering in a basic pH range (e.g., about pH 7 or 8 to 11, about pH 7 or 8 to 10, about pH 7 or 8 to 9, about pH 10-11, about pH 9-10, about pH 8-9, or about pH 7-8). Non-limiting examples of buffers or buffering agents that provide buffering in a basic pH range include borate, saline phosphate, saline sodium citrate, 2-(methylamino)succinic acid, N,N-bis(2-hydroxyethyl)glycine (bicine), N-tris(hydroxymethyl)methylglycine (tricine), tris(hydroxymethyl)methylamine (Tris), 2-(cyclohexylamino)ethanesulfonic acid (CHES), 4-(2-hydroxyethyl)-1-piperazineethanesulfonic acid (HEPES), piperazine-N,N'-bis(2-ethanesulfonic acid) (PIPES), 2-{[tris(hydroxymethyl)methyl]amino}ethanesulfonic acid (TES), 3-amino-1-propanesulfonic acid, 3-(cyclohexylamino)-1-propanesulfonic acid (CAPS), 3-(cyclohexylamino)-2-hydroxy-1-propanesulfonic acid (CAPSO), N-(2-hydroxyethyl)piperazine-N'-(3-propanesulfonic acid) (EPPS), 3-(N-morpholino)propanesulfonic acid (MOPS), 3-{[tris(hydroxymethyl)methyl]amino}-propanesulfonic acid (TAPS), 3-[N-tris(hydroxymethyl)methylamino]-2-hydroxypropanesulfonic acid (TAPSO), 4-(cyclohexylamino)-1-butanesulfonic acid (CABS), and analogs, derivatives and salts thereof.

The detergents can be denaturing detergents or non-denaturing detergents. Non-limiting examples of denaturing detergents and non-denaturing detergents include anionic surfactants, cationic surfactants, non-ionic surfactants, zwitterionic surfactants, ampholytic surfactants, benzethonium chloride, cetyltrimethylammonium bromide (CTAB), 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), N,N-dimethyldecylamine-N-oxide, guanidinium thiocyanate, hexadecyltrimethylammonium bromide, lithium dodecyl sulfate (LDS), sodium dodecyl sulfate (SDS), sodium lauryl sulfate, sodium cholate, sodium deoxycholate, ethoxylated fatty alcohol ethers, lauryl ethers, ethoxylated alkyl phenol compounds [e.g., ethoxylated nonyl phenol compounds, such as NP-40 (nonyl phenoxypolyethoxylethanol)], octylphenoxy polyethoxy ethanol compounds, modified oxyethylated straight-chain alcohols, modified oxypropylated straight-chain alcohols, polyethylene glycol mono-oleate compounds, polysorbate compounds (e.g., polyoxyethylene sorbitan monolaurate compounds, such as Polysorbates (Tweens) 20, 40, 60 and 80), phenolic fatty alcohol ethers, phenolic polyethylene glycols (e.g., Triton X-100), and analogs, derivatives and salts thereof.

Examples of chaotropes include without limitation formamide, guanidine and salts thereof (e.g., guanidinium hydrochloride), isothiocyanate, urea, and analogs, derivatives and salts thereof.

In some embodiments, the composition containing the biological material comprises an oxygen radical scavenger. In certain embodiments, the concentration of the oxygen radical scavenger by mass (mg) relative to the volume (µL) of the at least one alcohol solvent (or the at least one ionic organic solvent in other embodiments of a composition comprising a biological material in a substantially water-free fluid medium, as described below) is at least about 1%, 5%, 10%, 25%, 50%, 75%, 100%, 125%, 150%, 200%, 250% or 300%. In some embodiments, the concentration of the oxygen radical scavenger by mass (mg) relative to the volume (µL) of the at least one alcohol solvent (or the at least one ionic organic solvent in other embodiments) is about 25%-150%, 25%-125%, 25%400%, 25%-75% or 25%-50%.

In some embodiments, the composition comprises the biological material and an oxygen radical scavenger in ethylene glycol, 1,3-propanediol, glycerol or 1,2-butanediol, or any combination thereof. In certain embodiments, the oxygen radical scavenger is mannitol, mannose, sucrose or trehalose.

In further embodiments, the composition containing the biological material comprises one or more substances that enhance the stability of single-stranded and double-stranded polynucleotides containing RNA nucleotides and/or DNA nucleotides. In certain embodiments, the composition comprises: (a) a metal chelator, a hydroxyl radical scavenger, and an RNase inhibitor; or (b) a hydroxyl radical scavenger and a DNase inhibitor.

In additional embodiments, the composition containing the biological material comprises a metal salt, optionally in addition to one or more other substances described herein. The metal salt can enhance the stability and/or the solubility of the biological material in the substantially water-free fluid medium. As an example, the metal salt can increase the melting temperature of a double-stranded polynucleotide containing RNA nucleotides and/or DNA nucleotides. As another example, the metal salt can increase the solubility and the refolding yield, and can promote retention of the activity, of a protein (e.g., an enzyme) preserved in the substantially water-free fluid medium. In some embodiments, the metal salt comprises an $M^{+1}$ (or monovalent) salt or an $M^{+2}$ (or divalent) salt, or both. $M^{+1}$ (or monovalent) salts include without limitation lithium salts, sodium salts and potassium salts of fluoride, chloride, bromide, iodide, acetate, formate, nitrate, perchlorate ($ClO_4^-$), phosphate, sulfate, tetrafluoroborate ($BF_4^-$) and thiocyanate ($^-SCN$), and $M^{+2}$ (or divalent) salts include magnesium salts, manganese salts and calcium salts of fluoride, chloride, bromide, iodide, acetate, formate, nitrate, perchlorate, phosphate, sulfate, tetrafluoroborate and thiocyanate. In some embodiments, the metal salt comprises LiCl, NaCl, KCl, $MgCl_2$ or $MnCl_2$, or any combination thereof.

The biological material is soluble in the substantially water-free alcohol solvent, and thus may not need to be re-dissolved for use in fluid-phase reactions or assays, including nucleic acid amplification reactions based on PCR and analytical and diagnostic assays, such as immunoassays. In some embodiments, at least about 50%, 60%, 70%, 80%, 90%, 95% or 99% of the biological material by mass is dissolved in the substantially water-free alcohol solvent, e.g., after storage of the composition comprising the biological material in a closed container (e.g., a capped tube, vial or well) at a temperature from ambient temperature to about 40° C. for at least about 1 day, 3 days, week, 2 weeks, 3 weeks, 1 month, 2 months, 3 months, 6 months, 1 year, 1.5 years or 2 years. In certain embodiments, at least about 80% or 90% of the biological material by mass is dissolved in the substantially water-free alcohol solvent after storage of the composition comprising the biological material in a closed container (e.g., a capped tube, vial or well) at ambient temperature for at least about 3 months or 6 months.

Furthermore, the biological material is stable (e.g., retains its structural integrity) in the substantially water-free alcohol solvent at ambient temperature or higher, and thus does not need to be refrigerated or frozen during shipping or storage. In some embodiments, the biological material is stable (e.g., retains its structural integrity) in the substantially water-free alcohol solvent after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or years. In further embodiments, the biological material is resistant to irreversible hydrolytic damage, irreversible oxidative damage, and irreversible denaturation (e.g., irreversible unfolding or irreversible loss of secondary structure or tertiary structure) after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In certain embodiments, the biological material is resistant to irreversible hydrolytic damage, irreversible oxidative damage, and irreversible denaturation (e.g., irreversible unfolding or irreversible loss of secondary structure or tertiary structure) after storage of the composition comprising the biological material in a closed container (e.g., a capped tube, vial or well) at ambient temperature for at least about 3 months or 6 months.

In addition, the biological material retains its function or activity when it is preserved in the substantially water-free alcohol solvent at ambient temperature or higher and is tested for its function or activity under appropriate conditions (e.g., in an aqueous medium). In some embodiments, the biological material retains its function or activity after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In further embodiments, the biological material retains at least about 50%, 60%, 70%, 80%, 90%, 95% or 99% of its function or activity after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In certain embodiments, the biological material retains at least about 90% of its function or activity after storage of the composition comprising the biological material in a closed container (e.g., a capped tube, vial or well) at ambient temperature for at least about 3 months or 6 months. The function or activity of a biological material preserved in the substantially water-free alcohol solvent and tested at a particular time point can be compared to the function or activity of a positive control, e.g., the function or activity of the biological material prepared under appropriate conditions (e.g., in an aqueous medium) shortly before its use in the test protocol (e.g., test reaction or test assay).

Non-limiting examples of retention of a biological material's function or activity include: a polypeptide enzyme or a polynucleotide enzyme retaining its enzymatic or catalytic function or activity; a polypeptide retaining its ability to regulate (e.g., agonize or antagonize/inhibit) an enzyme; an antibody, a polypeptide aptamer or a polynucleotide aptamer retaining its binding affinity or specificity for a target antigen, ligand or analyte; a polypeptide ligand of an antibody retaining its ability to be recognized and bound by the antibody; a hormone or a cytokine retaining its biological function or activity; a polypeptide therapeutic retaining its pharmacological function or activity; a vaccine retaining its prophylactic or immune function or activity; a pair of forward and reverse primers retaining their ability to prime amplification of a target polydeoxyribonucleotide or a target nucleic acid (e.g., genetic) locus; a reverse transcription primer retaining its ability to prime reverse transcription of a target polyribonucleotide; a biological sample retaining its biological activity or its function as an analyte in an assay, or components in the biological sample retaining their biological activity or their function as analytes in an assay; and bacterial cells retaining their infectivity in an appropriate medium (e.g., an agar medium or a fluid culture), or viral particles retaining their infectivity in an appropriate medium (e.g., a natural fluid or a laboratory cell culture).

Method of Preserving a Biological Material in an Anhydrous, Non-Ionic Organic Solvent Further embodiments of the disclosure relate to a method of preserving a biological material in a substantially water-free, non-ionic organic solvent (e.g., an alcohol solvent). In some embodiments, the method comprises: mixing an aqueous mixture comprising a polypeptide, a polynucleotide or a biological sample, or any combination thereof, with at least one alcohol solvent to produce an aqueous organic mixture, wherein: the polypeptide comprises an enzyme that mediates a nucleic acid reaction, a polypeptide that regulates an enzyme, an antibody, a polypeptide ligand of an antibody, a polypeptide aptamer, a protein or enzyme useful for detection, a toxin, a hormone, a cytokine, a polypeptide therapeutic or a vaccine, or a derivative thereof or any combination thereof; the polynucleotide comprises a polynucleotide used in a nucleic acid reaction, a catalytic polynucleotide, or a polynucleotide that binds specifically to a target ligand, or a derivative thereof or any combination thereof; the biological sample comprises a biological fluid, a biological suspension, a fluid aspirate, blood, plasma, serum, lymph, cerebrospinal fluid, gastric fluid, bile, perspiration, ocular fluid, tears, oral fluid, sputum, saliva, a buccal sample, a tonsil sample, a nasal sample, mucus, a nasopharyngeal sample, semen, urine, a vaginal sample, a cervical sample, a rectal sample, a fecal sample, a wound or purulent sample, hair, a tissue, a tissue homogenate, cells, a cellular lysate, a tissue or cell biopsy, skin cells, tumor or cancer cells, a microbe, a pathogen, a bacterium, a fungus, a protozoan or a virus, or any combination thereof; and the at least one alcohol solvent is selected from the group consisting of linear and branched C2-C6 acyclic alcohols having one or more hydroxyl groups and C3-C6 cyclic alcohols having one or more hydroxyl groups and three to six ring carbon atoms, wherein the acyclic alcohols and the cyclic alcohols optionally comprise one or more halide atoms; and removing water from the aqueous organic mixture to produce a composition comprising the polypeptide, the polynucleotide or the biological sample, or any combination thereof, and the at least one alcohol solvent, wherein the composition is in a fluid state and is substantially free of water.

In some embodiments, the at least one alcohol solvent in the composition comprises no more than about 20%, 15%, 10%, 5%, 4%, 3%, 2%, 1% or 0.5% water by mass relative to the combined mass of water and the at least one alcohol solvent after removal of water from the aqueous organic mixture, and optionally after storage of the composition in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In certain embodiments, the at least one alcohol solvent in the composition comprises no more than about 10%, 5% or 1% water by mass relative to the combined mass of water and the at least one alcohol solvent after removal of water from the aqueous organic mixture, and optionally after storage of the composition in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In some embodiments, the at least one alcohol solvent in the composition comprises no more than about 10%, 5% or 1% water by mass relative to the combined mass of water and the at least one alcohol solvent after removal of water from the aqueous organic mixture and after storage of the composition in a closed container (e.g., a capped tube, vial or well) at ambient temperature for at least about 3 months or 6 months.

The at least one alcohol solvent can comprise one or more of any of the alcohol solvents described herein. Furthermore, the polypeptide, the polynucleotide or the biological sample, or any combination thereof, can comprise any polypeptide, any polynucleotide or any biological sample described herein.

In certain embodiments, water is removed from the aqueous organic mixture by evaporation. In further embodiments, removing water from the aqueous organic mixture to produce the composition in a fluid state does not pass through an intermediate solid state. In some embodiments, water is removed from the aqueous organic mixture at ambient temperature or at reduced temperature but above the freezing point of the aqueous organic mixture or the at least one alcohol solvent. In further embodiments, water is removed from the aqueous organic mixture at ambient pressure (e.g., at about 1 atm) or at reduced pressure (e.g., at about 0.1 atm, 0.2 atm, atm, 0.4 atm, or 0.5 atm or greater). In certain embodiments, water is removed from the aqueous organic mixture at ambient temperature and ambient pressure. In other embodiments, water is removed from the aqueous organic mixture at ambient temperature and reduced pressure. In yet other embodiments, water is removed from the aqueous organic mixture at reduced pressure and at reduced temperature but above the freezing point of the aqueous organic mixture or the at least one alcohol solvent. In further embodiments, water is removed from the aqueous organic mixture at a relative humidity of no more than about 60%, 50%, 40%, 30% or 20%.

The composition can be any composition comprising a biological material in a substantially water-free alcohol solvent as described herein. For example, the composition can comprise one or more substances as described herein, where the aqueous mixture, the at least one alcohol solvent or the aqueous organic mixture, or any combination thereof, can comprise the one or more substances (e.g., the one or more substances can be added to the aqueous mixture, the at least one alcohol solvent or the aqueous organic mixture, or any combination thereof). In certain embodiments, the one or more substances comprise: (a) a protease inhibitor; (b) an oxygen radical scavenger; (c) a metal chelator, a hydroxyl radical scavenger, and an RNase inhibitor; or (d) a hydroxyl radical scavenger and a DNase inhibitor. Furthermore, the composition can comprise a metal salt as described herein, where the aqueous mixture, the at least one alcohol solvent or the aqueous organic mixture, or any combination thereof, can comprise the metal salt (e.g., the metal salt can be added to the aqueous mixture, the at least one alcohol solvent or the aqueous organic mixture, or any combination thereof).

The composition can be re-hydrated by addition of an aqueous solution (e.g., water or an aqueous buffer) shortly before the composition is to be used in a biochemical reaction (e.g., PCR) or an analysis (e.g., an immunoassay).

Compositions Comprising a Biological Material in an Anhydrous, Ionic Organic Solvent Other embodiments of the disclosure relate to compositions comprising a biological material in a substantially water-free, ionic organic solvent. In some embodiments, such a composition comprises: a polypeptide, a polynucleotide or a biological sample, or any combination thereof, wherein the polypeptide comprises an enzyme that mediates a nucleic acid reaction, a polypeptide that regulates an enzyme, an antibody, a polypeptide ligand of an antibody, a polypeptide aptamer, a protein or enzyme useful for detection, a toxin, a hormone, a cytokine, a polypeptide therapeutic or a vaccine, or a derivative thereof or any combination thereof; wherein the polynucleotide comprises a polynucleotide used in a nucleic acid reaction, a catalytic polynucleotide, or a polynucleotide that binds specifically to a target ligand, or a derivative thereof or any combination thereof; and wherein the biological sample comprises a biological fluid, a biological suspension, a fluid aspirate, blood, plasma, serum, lymph, cerebrospinal fluid, gastric fluid, bile, perspiration, ocular fluid, tears, oral fluid, sputum, saliva, a buccal sample, a tonsil sample, a nasal sample, mucus, a nasopharyngeal sample, semen, urine, a vaginal sample, a cervical sample, a rectal sample, a fecal sample, a wound or purulent sample, hair, a tissue, a tissue homogenate, cells, a cellular lysate, a tissue or cell biopsy, skin cells, tumor or cancer cells, a microbe, a pathogen, a bacterium, a fungus, a protozoan or a virus, or any combination thereof; and at least one ionic organic solvent comprising an organic salt and an organic hydrogen bond donor; wherein the composition is in a fluid state and is substantially free of water.

In some embodiments, the at least one ionic organic solvent in the composition comprises no more than about 20%, 15%, 10%, 5%, 4%, 3%, 2%, 1% or 0.5% water by mass relative to the combined mass of water and the at least one ionic organic solvent, e.g., after storage of the composition in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In certain embodiments, the at least one ionic organic solvent in the composition comprises no more than about 10%, 5% or 1% water by mass relative to the combined mass of water and the at least one ionic organic solvent, e.g., after storage of the composition in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In some embodiments, the at least one ionic organic solvent in the composition comprises no more than about 10%, 5% or 1% water by mass relative to the combined mass of water and the at least one ionic organic solvent after storage of the composition in a closed container (e.g., a capped tube, vial or well) at ambient temperature for at least about 3 months or 6 months.

In further embodiments, the at least one ionic organic solvent is substantially soluble in water—e.g., at least about 50%, 60%, 70%, 80%, 90%, 95% or 99% of the at least one ionic organic solvent by mass or volume is soluble in water. In certain embodiments, at least about 90%, 95% or 99% of the at least one ionic organic solvent by mass or volume is soluble in water. In an embodiment, the at least one ionic organic solvent is miscible with water. Solubility of the at least one ionic organic solvent in water promotes transfer of a biological material from an aqueous medium to the at least one ionic organic solvent.

In yet further embodiments, the at least one ionic organic solvent has a boiling point substantially greater than that of water—e.g., a boiling point at least or greater than about 125° C., 150° C., 175° C., 200° C., 250° C. or 300° C. at a pressure of about 1 atm. In certain embodiments, the at least one ionic organic solvent has a boiling point at least or greater than about 150° C., 200° C. or 250° C. at a pressure of about 1 atm. The at least one ionic organic solvent having a boiling point greater than the boiling point of water allows for an aqueous mixture comprising a biological material to be mixed with at least one ionic organic solvent and for water to be selectively removed (e.g., by evaporation) from the resulting aqueous organic mixture without substantial loss of the at least one ionic organic solvent.

In additional embodiments, the at least one ionic organic solvent has a dynamic (or absolute) viscosity of no more than about 2000, 1500, 1000, 500, 400, 300, 200, 100, 50 or 25 centipoise (cP) or mPa·s at ambient temperature. In certain embodiments, the at least one ionic organic solvent has a dynamic (or absolute) viscosity of no more than about 1000, 500, 200, 100 or 50 cP or mPa·s at ambient temperature. A lower dynamic (or absolute) viscosity of the at least one ionic organic solvent allows for more facile handling of the composition comprising the biological material and the at least one ionic organic solvent (e.g., using a pipette or other means of transferring the composition).

In certain embodiments, the at least one ionic organic solvent is a eutectic solvent. In further embodiments, the at least one ionic organic solvent is a deep eutectic solvent.

In some embodiments, the molar ratio of the organic salt to the organic hydrogen bond donor in the at least one ionic organic solvent is from about 5:1 to about 1:5, or from about 4:1 to about 1:4, or from about 3:1 to about 1:3, or from about 2:1 to about 1:2, or from about 1.5:1 to about 1:1.5. In certain embodiments, the molar ratio of the organic salt to the organic hydrogen bond donor in the at least one ionic organic solvent is from about 1:1 to about 1:2, or is about 1:1, about 1:1.5 or about 1:2.

The organic salt of the at least one ionic organic solvent can be any organic salt capable of forming a solvent with an organic hydrogen bond donor (e.g., by heating a mixture of the organic salt and the organic hydrogen bond donor). In certain embodiments, the organic salt of the at least one ionic organic solvent comprises one or more organic salts selected from the group consisting of primary ammonium salts, secondary ammonium salts, tertiary ammonium salts, and quaternary ammonium salts. Examples of primary ammonium salts include without limitation methylammonium salts, ethylammonium salts, propylammonium salts, butylammonium salts, 2-hydroxyethylammonium salts, 2-acetylethylammonium salts, 2-chloroethylammonium salts, 2-fluoroethylammonium salts, and benzylammonium salts.

Non-limiting examples of secondary ammonium salts include dimethylammonium salts, diethylammonium salts, dipropylammonium salts, dibutylammonium salts, bis(2-hydroxyethyl)-ammonium salts, dibenzylammonium salts, ethylmethylammonium salts, (2-hydroxyethyl)methyl-ammonium salts, (2-hydroxyethyl)ethylammonium salts, (2-acetylethyl)methylammonium salts, (2-acetylethyl)ethylammonium salts, (2-chloroethyl)methylammonium salts, (2-chloroethyl)ethyl-ammonium salts, (2-fluoroethyl)methylammonium salts, (2-fluoroethyl)ethylammonium salts, benzylmethylammonium salts, benzylethylammonium salts, benzyl(2-hydroxyethyl)ammonium salts, benzyl(2-acetylethyl)ammonium salts, benzyl(2-chloroethyl)ammonium salts, and benzyl(2-fluoroethyl)ammonium salts.

Non-limiting examples of tertiary ammonium salts include trimethylammonium salts, triethylammonium salts, dimethylethylammonium salts, diethylmethylammonium salts, (benzyl)(ethyl)methylammonium salts, (benzyl)dimethylammonium salts, (benzyl)diethylammonium salts, (2-hydroxyethyl)dimethylammonium salts, (2-hydroxyethyl)diethylammonium salts, (2-acetylethyl)dimethylammonium salts, (2-acetylethyl)diethylammonium salts, (2-chloroethyl)-dimethylammonium salts, (2-chloroethyl)diethylammonium salts, (2-fluoroethyl)dimethyl-ammonium salts, (2-fluoroethyl)diethylammonium salts, (2-hydroxyethyl)(benzyl)methylammonium salts, (2-hydroxyethyl)(benzyl)ethylammonium salts, (2-acetylethyl) (benzyl)methylammonium salts, (2-acetylethyl)(benzyl)ethylammonium salts, (2-chloroethyl)(benzyl)methylammonium salts, (2-chloroethyl)(benzyl)ethylammonium salts, (2-fluoroethyl)(benzyl)methylammonium salts, (2-fluoroethyl)(benzyl)ethylammonium salts, [bis(2-hydroxyethyl)]methylammonium salts, [bis(2-hydroxyethyl)]ethylammonium salts, and [bis(2-hydroxyethyl)]benzylammonium salts.

Examples of quaternary ammonium salts include without limitation tetramethylammonium salts, tetraethylammonium salts, (2-hydroxyethyl)trimethylammonium (choline) salts, (2-hydroxyethyl)triethylammonium salts, (2-acetylethyl)trimethylammonium salts, (2-acetylethyl)-triethylammonium salts, (2-chloroethyl)trimethylammonium salts, (2-chloroethyl)triethylammonium salts, (2-fluoroethyl)trimethylammonium salts, (2-fluoroethyl)triethylammonium salts, (benzyl)(dimethyl)(2-hydroxyethyl)ammonium salts, (benzyl)(dimethyl)(2-acetylethyl)ammonium salts, (benzyl)(dimethyl)(2-chloroethyl)ammonium salts, (benzyl)(dimethyl)(2-fluoroethyl)-ammonium salts, (benzyl)(diethyl)(2-hydroxyethyl)ammonium salts, (benzyl)(diethyl)(2-acetylethyl)ammonium salts, (benzyl)(diethyl)(2-chloroethyl)ammonium salts, (benzyl)(diethyl)(2-fluoroethyl)ammonium salts, [bis(2-hydroxyethyl)]dimethylammonium salts, [bis(2-hydroxyethyl)]-diethylammonium salts, [bis(2-hydroxyethyl)](benzyl)(methyl)ammonium salts, [bis(2-hydroxyethyl)](benzyl)(ethyl)ammonium salts, (dimethyl)(ethyl)(2-hydroxyethyl) ammonium salts, (diethyl)(methyl)(2-hydroxyethyl) ammonium salts, (benzyl)trimethylammonium salts, and (benzyl)triethylammonium salts.

The anion of the organic salt can be any anion capable of interacting (e.g., complexing or hydrogen bonding) with an organic hydrogen bond donor. In some embodiments, the anion of the organic salt is a monovalent anion. In certain embodiments, the anion of the organic salt (e.g., the primary ammonium salts, the secondary ammonium salts, the tertiary ammonium salts, and the quaternary ammonium salts described herein) is fluoride, chloride, bromide, iodide, acetate, formate, nitrate, perchlorate (ClO4-), phosphate, sulfate, tetrafluoroborate (BF4-), or thiocyanate (—SCN).

In some embodiments, the organic salt comprises a quaternary ammonium salt. In certain embodiments, the organic salt comprises a (2-hydroxyethyl)trimethylammonium (choline) salt. In further embodiments, the organic salt comprises choline chloride or choline acetate.

The organic hydrogen bond donor of the at least one ionic organic solvent can be any organic hydrogen bond donor capable of forming a solvent with an organic salt, or any organic hydrogen bond donor capable of interacting (e.g., complexing or hydrogen bonding) with the anion of an organic salt. In certain embodiments, the organic hydrogen bond donor of the at least one ionic organic solvent comprises one or more organic hydrogen bond donors selected from the group consisting of urea compounds, thiourea compounds, carbamates, amides, carboxylic acids, phenolic compounds, acyclic alcohols, and cyclic alcohols.

Non-limiting examples of urea compounds and thiourea compounds include urea, N-methylurea, N,N'-dimethylurea, N,N-dimethylurea, N,N,N'-trimethylurea, thiourea, N-methylthiourea, N,N'-dimethylthiourea, N,N-dimethylthiourea, and N,N,N'-trimethylthiourea. In an embodiment, the organic hydrogen bond donor comprises urea.

Examples of carbamates include without limitation methyl carbamate, ethyl carbamate, propyl carbamate, butyl carbamate, methyl N-methylcarbamate, ethyl N-methylcarbamate, propyl N-methylcarbamate, and butyl N-methylcarbamate. Examples of amides include without limitation acetamide, propanamide, butanamide, pentanamide, benzamide, N-methylacetamide, methylpropanamide, N-methylbutanamide, N-methylpentanamide, and N-methylbenzamide. In an embodiment, the organic hydrogen bond donor comprises acetamide.

Non-limiting examples of carboxylic acids include adipic acid, benzoic acid, citric acid, ethylenediaminetetraacetic acid, fumaric acid, maleic acid, malonic acid, oxalic acid, phenylacetic acid, phenylpropionic acid, propane-1,2,3-tricarboxylic acid (tricarballylic acid), succinic acid, and tartaric acid. In certain embodiments, the organic hydrogen bond donor comprises citric acid, malonic acid or oxalic acid, or any combination thereof. Examples of phenolic compounds include without limitation phenol and tyrosine.

Examples of acyclic alcohols include without limitation the linear and branched C2-C6 acyclic alcohols having one or more hydroxyl groups and optionally comprising one or more halide atoms described herein. Examples of cyclic alcohols include without limitation ascorbic acid and the C3-C6 cyclic alcohols having one or more hydroxyl groups and three to six ring carbon atoms and optionally comprising one or more halide atoms described herein. In certain embodiments, the organic hydrogen bond donor comprises ethylene glycol, 1,2-propanediol, 1,3-propanediol, glycerol, 1,2-butanediol, 1,3-butanediol, 1,4-butanediol, 2,3-butanediol, 1,2,4-butanetriol or 1,5-pentanediol, or any combination thereof. In further embodiments, the organic hydrogen bond donor comprises ethylene glycol, 1,3-propanediol, glycerol or 1,2-butanediol, or any combination thereof.

Examples of ionic organic solvents include without limitation: choline chloride or ethylammonium chloride and urea; choline chloride or ethylammonium chloride and acetamide; choline chloride or ethylammonium chloride and citric acid; choline chloride or ethylammonium chloride and malonic acid; choline chloride or ethylammonium chloride and oxalic acid; choline chloride or ethylammonium chloride and ethylene glycol; choline chloride or ethylammonium chloride and glycerol; and choline chloride or ethylammonium chloride and 1,2-butanediol.

The at least one ionic organic solvent can be prepared by any method known in the art. For example, the at least one ionic organic solvent can be prepared by heating at elevated temperature (e.g., at about 50° C., 75° C. or 100° C. or higher) a mixture comprising one or more organic salts and one or more organic hydrogen bond donors with stirring to produce a liquid (e.g., a homogeneous liquid). An organic salt having a melting point above ambient temperature, and/or an organic hydrogen bond donor having a melting point above ambient temperature, can be used to prepare the at least one ionic organic solvent.

The composition can comprise in the substantially water-free ionic organic solvent any polypeptide, any polynucleotide or any biological sample, or any combination thereof, described herein. To enhance, e.g., the stability and/or the solubility of the biological material in the substantially water-free ionic organic solvent, the composition can further comprise a metal salt, and/or one or more substances selected from the group consisting of reducing agents, antioxidants, free radical scavengers, oxygen radical scavengers, hydroxyl radical scavengers, singlet oxygen quenchers, hydroperoxide-removing agents, protease inhibitors, nuclease inhibitors, ribonuclease (RNase) inhibitors, deoxyribonuclease (DNase) inhibitors, metal chelators, preservatives, anti-microbials, buffers (or buffering agents), detergents, and chaotropes, as described herein. In certain embodiments, the composition comprises the biological material and: a protease inhibitor; an oxygen radical scavenger; a metal chelator, a hydroxyl radical scavenger, and an RNase inhibitor; or a hydroxyl radical scavenger and a DNase inhibitor.

The biological material is soluble in the substantially water-free ionic organic solvent, and thus may not need to be re-dissolved for use in fluid-phase reactions or assays, including nucleic acid amplification reactions based on PCR and analytical and diagnostic assays, such as immunoassays. In some embodiments, at least about 50%, 60%, 70%, 80%, 90%, 95% or 99% of the biological material by mass is dissolved in the substantially water-free ionic organic solvent, e.g., after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In certain embodiments, at least about 80% or 90% of the biological material by mass is dissolved in the substantially water-free ionic organic solvent after storage of the composition comprising the biological material in a closed container (e.g., a capped tube, vial or well) at ambient temperature for at least about 3 months or 6 months.

Furthermore, the biological material is stable (e.g., retains its structural integrity) in the substantially water-free ionic organic solvent at ambient temperature or higher, and thus does not need to be refrigerated or frozen during shipping or storage. In some embodiments, the biological material is stable (e.g., retains its structural integrity) in the substantially water-free ionic organic solvent after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In further embodiments, the biological material is resistant to irreversible hydrolytic damage, irreversible oxidative damage, and irreversible denaturation (e.g., irreversible unfolding or irreversible loss of secondary structure or tertiary structure) after storage of the composition comprising the biological material in a closed container (e.g., a capped tube, vial or well) at a temperature from ambient temperature to about 40° C. for at least about 1 day, 3 days, week, 2 weeks, 3 weeks, 1 month, 2 months, 3 months, 6 months, 1 year, 1.5 years or 2 years. In certain embodiments, the biological material is resistant to irreversible hydrolytic damage, irreversible oxidative damage, and irreversible denaturation (e.g., irreversible unfolding or irreversible loss of secondary structure or tertiary structure) after storage of the composition comprising the biological material in a closed container (e.g., a capped tube, vial or well) at ambient temperature for at least about 3 months or 6 months.

In addition, the biological material retains its function or activity when it is preserved in the substantially water-free ionic organic solvent at ambient temperature or higher and is tested for its function or activity under appropriate conditions (e.g., in an aqueous medium). In some embodiments, the biological material retains its function or activity after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In further embodiments, the biological material retains at least about 50%, 60%, 70%, 80%, 90%, 95% or 99% of its function or activity after storage of the composition comprising the biological material in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In certain embodiments, the biological material retains at least about 90% of its function or activity after storage of the composition comprising the biological material in a closed container (e.g., a capped tube, vial or well) at ambient temperature for at least about 3 months or 6 months. The function or activity of a biological material preserved in the substantially water-free ionic organic solvent and tested at a particular time point can be compared to the function or activity of a positive control, e.g., the function or activity of the biological material prepared under appropriate conditions (e.g., in an aqueous medium) shortly before its use in the test protocol (e.g., test reaction or test assay).

Method of Preserving a Biological Material in an Anhydrous, Ionic Organic Solvent Additional embodiments of the disclosure relate to a method of preserving a biological material in a substantially water-free, ionic organic solvent. In some embodiments, the method comprises: mixing an aqueous mixture comprising a polypeptide, a polynucleotide or a biological sample, or any combination thereof, with at least one ionic organic solvent to produce an aqueous organic mixture, wherein the polypeptide comprises an enzyme that mediates a nucleic acid reaction, a polypeptide that regulates an enzyme, an antibody, a polypeptide ligand of an antibody, a polypeptide aptamer, a protein or enzyme useful for detection, a toxin, a hormone, a cytokine, a polypeptide therapeutic or a vaccine, or a derivative thereof or any combination thereof; the polynucleotide comprises a polynucleotide used in a nucleic acid reaction, a catalytic polynucleotide, or a polynucleotide that binds specifically to a target ligand, or a derivative thereof or any combination thereof; the biological sample comprises a biological fluid, a biological suspension, a fluid aspirate, blood, plasma, serum, lymph, cerebrospinal fluid, gastric fluid, bile, perspiration, ocular fluid, tears, oral fluid, sputum, saliva, a buccal sample, a tonsil sample, a nasal sample, mucus, a nasopharyngeal sample, semen, urine, a vaginal sample, a cervical sample, a rectal sample, a fecal sample, a wound or purulent sample, hair, a tissue, a tissue homogenate, cells, a cellular lysate, a tissue or cell biopsy, skin cells, tumor or cancer cells, a microbe, a pathogen, a bacterium, a fungus, a protozoan or a virus, or any combination thereof; and the at least one ionic organic solvent comprises an organic salt and an organic hydrogen bond donor; and removing water from the aqueous organic mixture to produce a composition comprising the polypeptide, the polynucleotide or the biological sample, or any combination thereof, and the at least one ionic organic solvent, wherein the composition is in a fluid state and is substantially free of water.

In some embodiments, the at least one ionic organic solvent in the composition comprises no more than about 20%, 15%, 10%, 5%, 4%, 3%, 2%, 1% or 0.5% water by mass relative to the combined mass of water and the at least one ionic organic solvent after removal of water from the aqueous organic mixture, and optionally after storage of the composition in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In certain embodiments, the at least one ionic organic solvent in the composition comprises no more than about 10%, 5% or 1% water by mass relative to the combined mass of water and the at least one ionic organic solvent after removal of water from the aqueous organic mixture, and optionally after storage of the composition in a closed container (e.g., a capped tube, vial or well) at a temperature from ambient temperature to about 40° C. for at least about 1 day, 3 days, 1 week, 2 weeks, 3 weeks, 1 month, 2 months, 3 months, 6 months, 1 year, 1.5 years or 2 years. In some embodiments, the at least one ionic organic solvent in the composition comprises no more than about 10%, 5% or 1% water by mass relative to the combined mass of water and the at least one ionic organic solvent after removal of water from the aqueous organic mixture and after storage of the composition in a closed container (e.g., a capped tube, vial or well) at ambient temperature for at least about 3 months or 6 months.

The at least one ionic organic solvent can comprise any ionic organic solvent described herein. Furthermore, the polypeptide, the polynucleotide or the biological sample, or any combination thereof, can comprise any polypeptide, any polynucleotide or any biological sample described herein.

In certain embodiments, water is removed from the aqueous organic mixture by evaporation. In further embodiments, removing water from the aqueous organic mixture to produce the composition in a fluid state does not pass through an intermediate solid state. In some embodiments, water is removed from the aqueous organic mixture at ambient temperature or at reduced temperature but above the freezing point of the aqueous organic mixture or the at least one ionic organic solvent. In further embodiments, water is removed from the aqueous organic mixture at ambient pressure (e.g., at about 1 atm) or at reduced pressure (e.g., at about 0.1 atm, 0.2 atm, 0.3 atm, 0.4 atm, or 0.5 atm or greater). In certain embodiments, water is removed from the aqueous organic mixture at ambient temperature and ambient pressure. In other embodiments, water is removed from the aqueous organic mixture at ambient temperature and reduced pressure. In yet other embodiments, water is removed from the aqueous organic mixture at reduced pressure and at reduced temperature but above the freezing point of the aqueous organic mixture or the at least one ionic organic solvent. In further embodiments, water is removed from the aqueous organic mixture at a relative humidity of no more than about 60%, 50%, 40%, 30% or 20%.

The composition can be any composition comprising a biological material in a substantially water-free ionic organic solvent as described herein. For example, the composition can comprise one or more substances as described herein, where the aqueous mixture, the at least one ionic organic solvent or the aqueous organic mixture, or any combination thereof, can comprise the one or more substances (e.g., the one or more substances can be added to the aqueous mixture, the at least one ionic organic solvent or the aqueous organic mixture, or any combination thereof). In certain embodiments, the one or more substances comprise: (a) a protease inhibitor; (b) an oxygen radical scavenger; (c) a metal chelator, a hydroxyl radical scavenger, and an RNase inhibitor; or (d) a hydroxyl radical scavenger and a DNase inhibitor. Furthermore, the composition can comprise a metal salt as described herein, where the aqueous mixture, the at least one ionic organic solvent or the aqueous organic mixture, or any combination thereof, can comprise the metal salt (e.g., the metal salt can be added to the aqueous mixture, the at least one ionic organic solvent or the aqueous organic mixture, or any combination thereof).

The composition can be re-hydrated by addition of an aqueous solution (e.g., water or an aqueous buffer) shortly before the composition is to be used in a biochemical reaction (e.g., PCR) or an analysis (e.g., an immunoassay).

Containers and Kits Comprising Biological Materials in Anhydrous Fluid Media

Further embodiments of the disclosure relate to containers and kits containing compositions comprising biological and biological materials in substantially water-free fluid media. A container can comprise any composition comprising a biological material in a substantially water-free fluid medium described herein. The container can be any vessel suitable for holding or storing a fluid composition. In certain embodiments, the container is a tube, a vial, a well or a chamber (including a well or chamber in a cartridge). In further embodiments, the container is any vessel suitable for keeping away moisture during storage of a composition, such as a capped tube, vial, well or chamber. A capped container can have any suitable cap, such as a snap-on cap or a screw cap. In certain embodiments, the container is a screw-cap tube or a screw-cap vial. A screw-cap tube or a screw-cap vial can have a gasket for improved sealing of the screw cap to the tube or the vial.

A kit can contain one or more compositions comprising a biological material in a substantially water-free fluid medium described herein. The kit can contain one or more containers comprising one or more compositions, as described herein. For example, a kit can contain reagents for performing a biochemical reaction (e.g., a nucleic acid amplification reaction, such as PCR or RT-PCR) or an assay (e.g., an immunoassay, such as an ELISA or a sandwich immunoassay), wherein: the kit can include a container containing a composition comprising all the reagents for performing the biochemical reaction or the assay; or the kit can include two or more containers, where each container contains a composition comprising one or more reagents for performing the biochemical reaction or the assay as described herein, and the one or more reagents in each of the containers can be combined prior to or at the time of their use in the biochemical reaction or the assay or can be used at different times in performing the biochemical reaction or the assay as appropriate.

If an antibody used in an immunoassay is conjugated to a detection enzyme, the kit can further comprise a substrate with which the enzyme can react to produce a detectable signal (e.g., a color change in the substrate).

As an example, a kit can comprise reagents for performing PCR or RT-PCR, wherein: the kit can include a container containing a composition comprising all the reagents for performing PCR or RT-PCR; or the kit can include two or more containers, where each container contains a composition comprising one or more reagents for performing PCR or RT-PCR as described herein (e.g., a DNA polymerase in one container and at least one pair of forward and reverse primers in a separate container for PCR, or a reverse transcriptase and a DNA polymerase in one container and at least one reverse transcription primer and at least one pair of forward and reverse primers in a separate container for RT-PCR), and the one or more reagents in each of the containers can be combined prior to or at the time of their use in PCR or RT-PCR.

As another example, a kit can comprise reagents for performing an ELISA or a sandwich immunoassay, wherein: the kit can include two or more containers, each container containing a composition comprising one or more reagents for performing the ELISA or the sandwich immunoassay as described herein (e.g., a first antibody in one container and a second antibody in a separate container for an ELISA or a sandwich immunoassay); and the one or more reagents in each of the containers can be used at different times in performing the ELISA or the sandwich immunoassay as appropriate (e.g., the second antibody can be used subsequent to use of the first antibody in the ELISA or the sandwich immunoassay).

A kit can further comprise water or an aqueous solution (e.g., an aqueous buffer) in a container (e.g., a vial, bottle or cartridge) for re-hydration of the biological material in a composition for use, e.g., in a reaction (e.g., a PCR amplification reaction) or an assay (e.g., an analytical or diagnostic assay, such as an immunoassay) which is performed in an aqueous medium. In addition, a kit can comprise a desiccant for promoting preservation of the biological material in a substantially anhydrous state. Non-limiting examples of desiccants include activated alumina, aerogel, silica gel, benzophenone, calcium chloride, calcium sulfate, cobalt chloride, copper sulfate, lithium chloride, lithium bromide, magnesium chloride, magnesium perchlorate, magnesium sulfate, potassium carbonate, sodium chlorate, sodium chloride, sodium hydroxide, sodium sulfate, sucrose, clay (e.g., bentonite clay and montmorillonite clay), and molecular sieves. Moreover, a kit can comprise instruction for storing and using a composition, and optionally instruction for using water or an aqueous solution (e.g., an aqueous buffer) to re-hydrate the biological material in a composition.

EXAMPLES

The following examples are intended only to illustrate the disclosure. Other procedures, methodologies, techniques, conditions and reagents may alternatively be used as appropriate.

Example 1: Preservation of RT-PCR Reagents in Glycerol for Human 18S rRNA Analysis An undiluted volume (about 25 µL) of the Master Mix of the Ag-Path ID™ One-Step RT-PCR Kit (Life Technologies) for analysis of human 18S ribosomal RNA (rRNA) was placed in a PCR tube. The volume of Master Mix contained some amount (e.g., about 0.5-4 µL) of glycerol. Varying amounts of sucrose (0 mg, or about 1.3 mg, 2.5 mg or 5 mg) were added to the Master Mix. Water was removed from the resulting mixture by evaporation at reduced pressure (about 0.2 atm) and ambient temperature overnight to yield a fluid mixture having a volume of about 4 µL. The evaporated mixture containing the RT-PCR reagents and optionally sucrose in glycerol was stored in the PCR tube capped with a snap-on cap at ambient temperature (about 25° C.) for varying periods of time (about 0 day, 7 days or 14 days).

For analysis of human 18S rRNA, nuclease-free water and template RNA (about 10 ng of HeLa total RNA) were added to the evaporated mixture in the PCR tube to a final volume of about 25 µL. Reverse transcription PCR was performed according to the manufacturer's recommended protocol. Production of the target 18S rRNA amplicon product having about 313 base pairs (bp) was analyzed by gel electrophoresis using 2% agarose gel and UV visualization. Positive control was the Master Mix not treated with sucrose and not subjected to water removal, where the Master Mix was prepared by taking unmixed RT-PCR reagents out of a −20° C. freezer and mixing them shortly before use at all tested time points (untreated and unevaporated Master Mix), with addition of the template RNA. Negative control was untreated and unevaporated Master Mix without addition of the template RNA.

Preservation of the reagents was assessed by electrophoresis of the RT-PCR products at time=0, about 7 days or about 14 days of storage (FIG. 1). When RT-PCR was performed shortly after preparation of the evaporated mixture (t=0), the target 313 bp 18S rRNA product was produced if no sucrose or about 1.3 mg, 2.5 mg or 5 mg of sucrose had been added to the RT-PCR Master Mix. When RT-PCR was performed after about 7 days of storage of the evaporated mixture at ambient temperature (t=7 days), addition of no sucrose to the Master Mix yielded a much lower amount of the target 313 bp product compared to addition of about 1.3 mg, 2.5 mg or 5 mg of sucrose to the Master Mix. When RT-PCR was performed after about 14 days of storage of the evaporated mixture at ambient temperature (t=14 days), addition of no sucrose or about 1.3 mg of sucrose to the Master Mix resulted in no detectable target 313 bp product, whereas addition of about 2.5 mg or 5 mg of sucrose to the Master Mix produced the target 313 bp product.

Figure 2A:
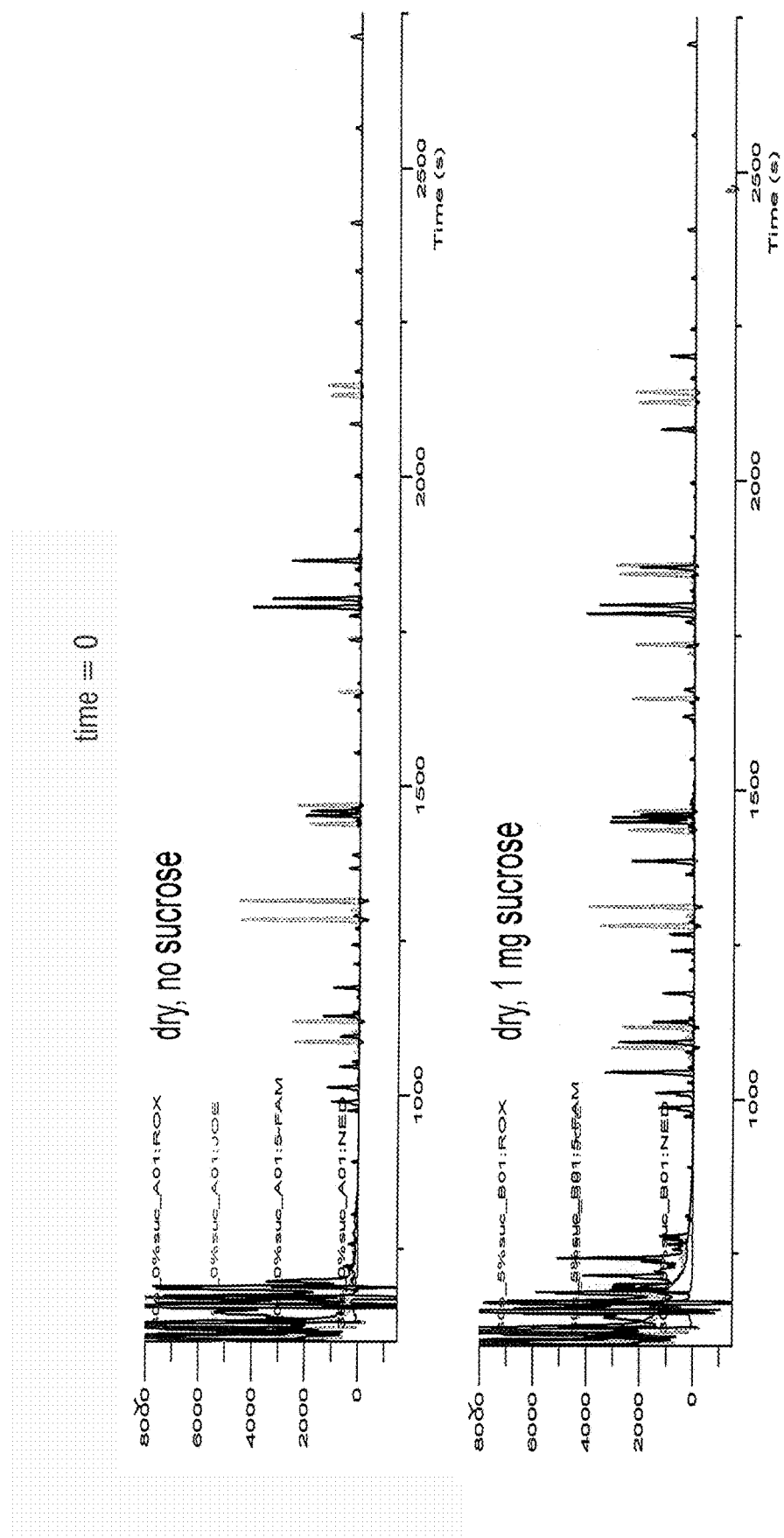
FIGS. 2 (A-B) shows electropherograms of multiplex PCR for analysis of all 13 short tandem repeat (STR) loci utilized in the CODIS forensic database, as well as Penta D, Penta E and amelogenin, after preservation of PCR reagents in glycerol, with addition of no sucrose or varying amounts of sucrose, at ambient temperature at time=0.
Figure 2B:
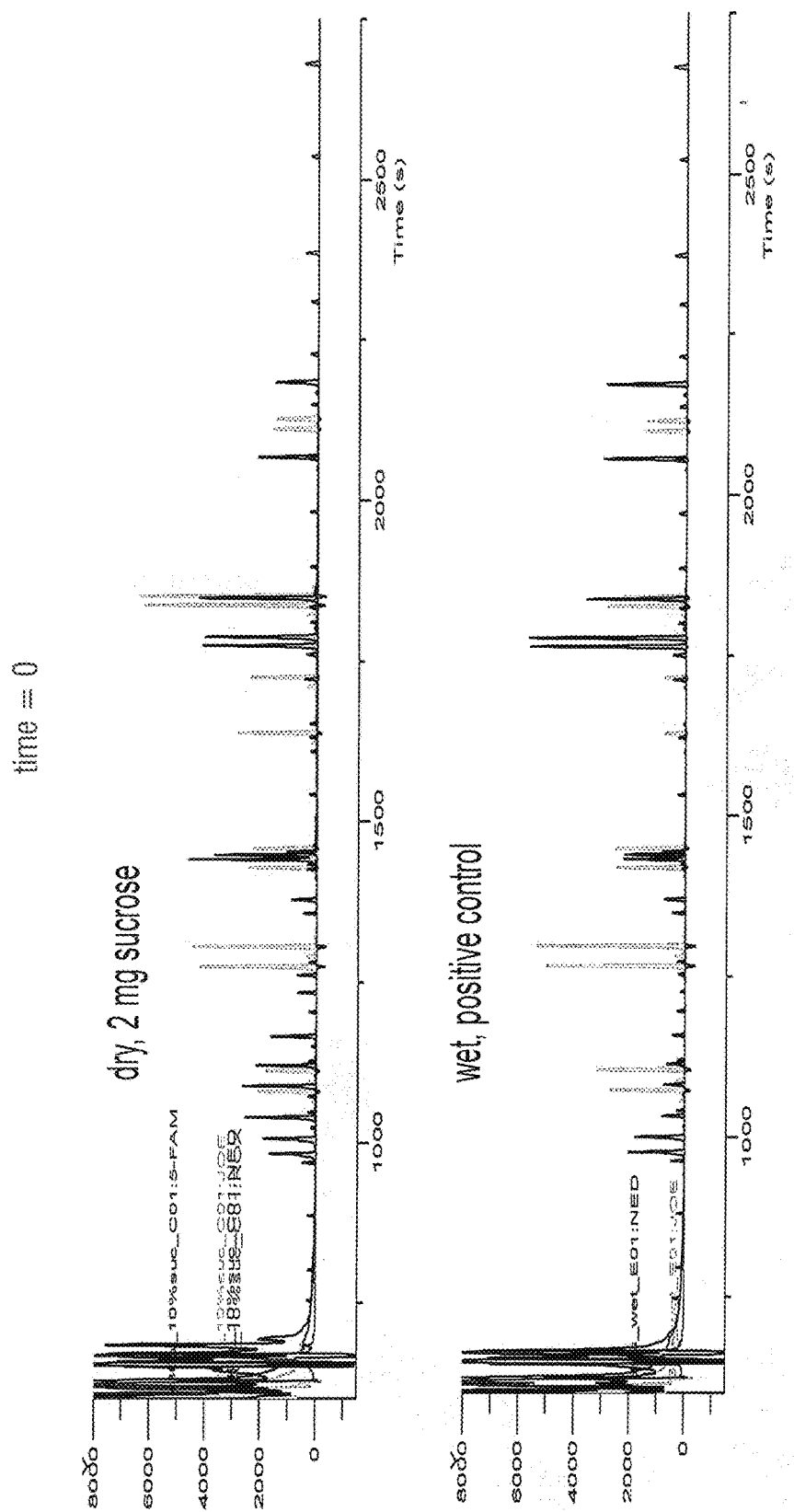
Figure 3A:
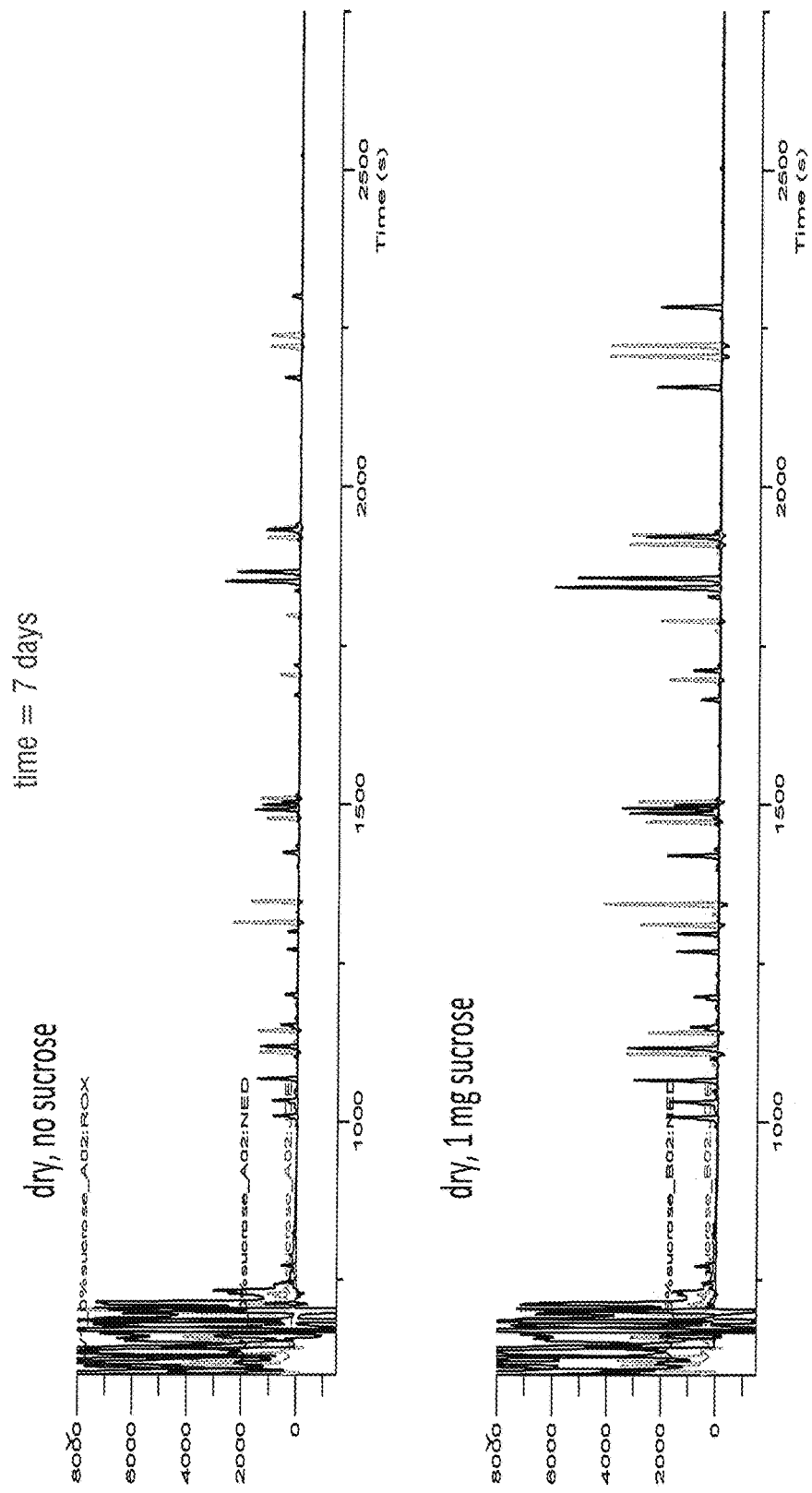
FIG. 3 (A-B) shows electropherograms of multiplex PCR for analysis of all 13 short tandem repeat (STR) loci utilized in the CODIS forensic database, as well as Penta D, Penta E and amelogenin, after preservation of PCR reagents in glycerol, with addition of no sucrose or varying amounts of sucrose, at ambient temperature after 7 days.
Figure 3B:
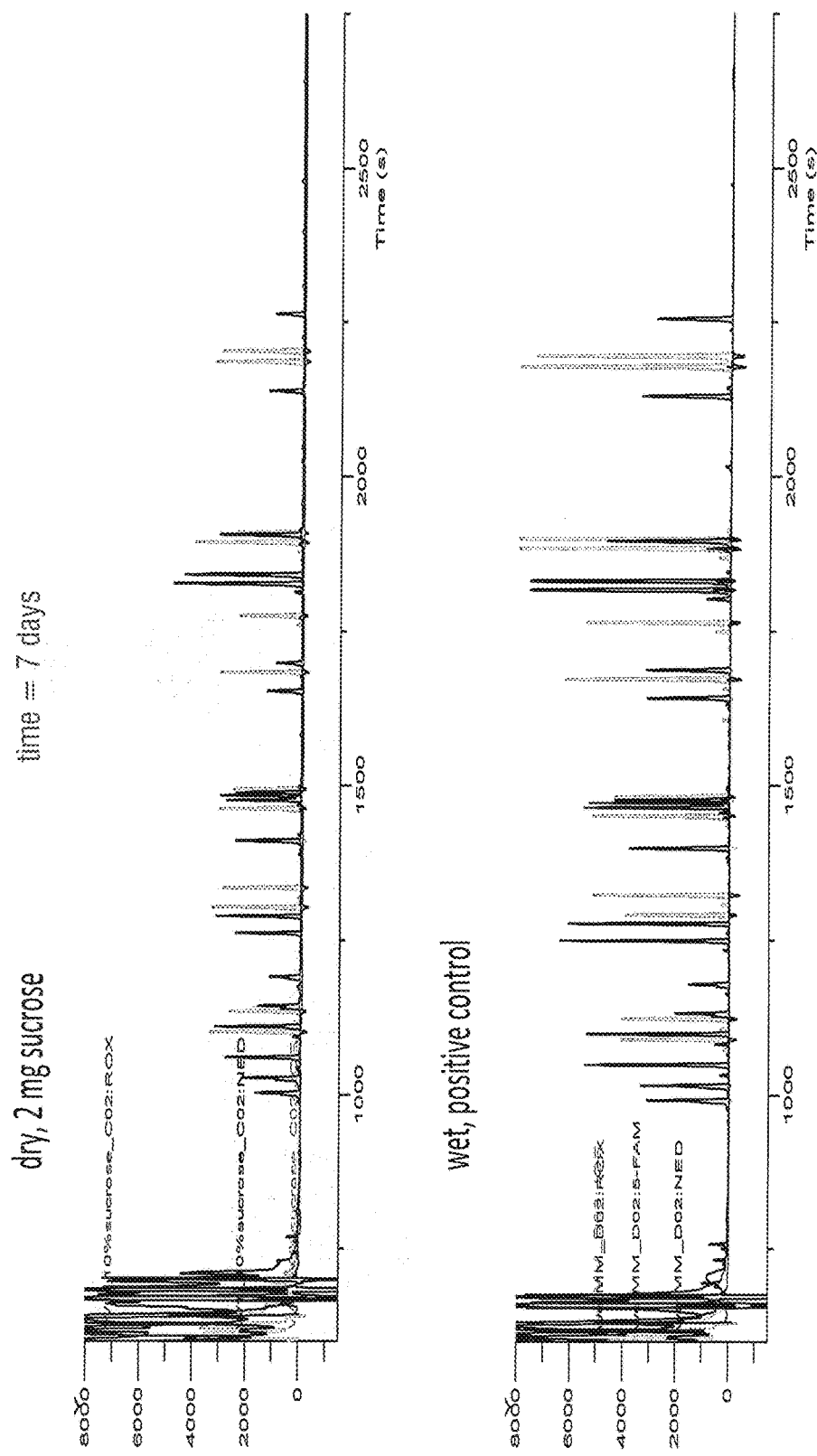

Example 2: Preservation of RT-PCR Reagents in Gycerol for Avian Flu Virus RNA Analysis An undiluted volume (about 25 t L) of the RT-PCR Master Mix of the TaqMan® Avian Influenza Virus (AIV-M) Reagents (Life Technologies) for analysis of AIV matrix (AIV-M) RNA was placed in a well of a 96-well optical PCR plate. The volume of Master Mix contained some amount (e.g., about 0.5-4 μL) of glycerol. Varying amounts of sucrose (0 mg, or about 1.3 mg or 2.5 mg) were added to the Master Mix. Water was removed from the resulting mixture by evaporation at reduced pressure (about 0.2 atm) and ambient temperature overnight to yield a fluid mixture having a volume of about 4 μL. The evaporated mixture containing the RT-PCR reagents and optionally sucrose in glycerol was stored in the well capped with a snap-on cap at ambient temperature (about 25° C.) for varying periods of time (about 0 day or 7 days). The PCR plate was kept in the dark during storage to protect a dye-labeled probe in the RT-PCR reagents from light.

For analysis of avian influenza virus matrix RNA, deionized nuclease-free water and template RNA (about 10 ng of AIV genomic RNA) were added to the evaporated mixture in the well to a final volume of about 25 μL. Reverse transcription PCR was performed according to the manufacturer's recommended protocol. Production of the target amplicon product of the matrix (M) gene of AIV was analyzed using an Applied Biosystems 7500 Fast Real-Time PCR System (Life Technologies), which generated Ct values when a fluorescent signal reached a level detectable by the real-time PCR instrument. Positive control was the Master Mix not treated with sucrose and not subjected to water removal, where the Master Mix was prepared by taking unmixed RT-PCR reagents out of a −20° C. freezer and mixing them shortly before use at all tested time points untreated and unevaporated Master Mix), with addition of the template RNA. Negative control was untreated and unevaporated Master Mix without addition of the template RNA.

Table 1 shows results when reverse transcription PCR was performed at time=0 or after about 7 days of storage. When RT-PCR was performed shortly after preparation of the evaporated mixture (t=0), addition of no sucrose to the RT-PCR Master Mix yielded a slightly lower amount of the target matrix product compared to addition of about 1.3 mg or 2.5 mg of sucrose to the Master Mix. When RT-PCR was performed after about 7 days of storage of the evaporated mixture at ambient temperature (t=7 days), addition of no sucrose to the Master Mix resulted in no detectable target matrix product, while addition of about 1.3 mg of sucrose to the Master Mix produced a lower amount of the target matrix product than addition of about 2.5 mg of sucrose to the Master Mix.

TABLE 1

Results of RT-PCR

| | time = 0 | | | time = 7 days | | |
|---|---|---|---|---|---|---|
| | Ct | Ave. Ct | Δ Ave. Ct (vs. pos. control) | Ct | Ave. Ct | Δ Ave. Ct (vs. pos. control) |
| Positive control (wet) | 25.02<br>25.64 | 25.33 | — | 24.92<br>24.86 | 24.89 | — |
| No sucrose (dry) | 27.00<br>26.77 | 26.89 | 1.56 | >>35<br>>>35 | | |
| 1.3 mg sucrose (dry) | 26.07<br>25.75 | 25.91 | 0.58 | 36.22<br>32.47 | 34.34 | 9.45 |
| 2.5 mg sucrose (dry) | 25.85<br>25.40 | 25.63 | 0.30 | 27.72<br>26.37 | 27.04 | 2.15 |
| Negative control (wet) | >>35 | | | >>35 | | |

Example 3: Preservation of PCR Reagents in Gycerol for STR-Based Human Identification An undiluted volume (about 20 μL) of the Master Mix of the PowerPlex® 16 HS System (Promega) for human identification was placed in a PCR tube. The volume of Master Mix contained some amount (e.g., about 0.5-4 μL) of glycerol. The Master Mix contained 16 different pairs of forward and reverse primers for amplifying all 13 current CODIS STR loci, as well as Penta D, Penta E and amelogenin. Each primer was labeled with a fluorescent dye, and a total of three different fluorescent dyes were used to label the 16 different pairs of forward and reverse primers. Varying amounts of sucrose (0 mg, or about 1 mg or 2 mg) were added to the Master Mix. Water was removed from the resulting mixture by evaporation at reduced pressure (about 0.2 atm) and ambient temperature overnight to yield a fluid mixture having a volume of about 4 μL. The evaporated mixture containing the PCR reagents and optionally sucrose in glycerol was stored in the PCR tube capped with a snap-on cap at ambient temperature (about 25° C.) for varying periods of time (about 0 day or 7 days). The PCR tube was kept in the dark during storage to protect the dye-labeled primers from light.

For analysis of the 13 CODIS STR loci, Penta D, Penta E and amelogenin, nuclease-free water and template DNA (about 1 ng of human genomic DNA) were added to the evaporated mixture in the PCR tube to a final volume of about 20 μL. Multiplex PCR was performed according to the manufacturer's recommended protocol. Production of the amplicon products of the 16 loci was analyzed using an Applied Biosystems 3130 Genetic Analyzer instrument (Life Technologies). Positive control was the Master Mix not treated with sucrose and not subjected to water removal, where the Master Mix was prepared by taking unmixed PCR reagents out of a −20° C. freezer and mixing them shortly before use at all tested time points (untreated and unevaporated Master Mix), with addition of the template DNA. Negative control was untreated and unevaporated Master Mix without addition of the template DNA.

Electropherograms generated by amplicon product analysis of multiplex PCR products performed at time=0 or after about 7 days of storage are shown in FIGS. 2 and 3, respectively. When PCR was performed shortly after preparation of the evaporated mixture (t=0), addition of no sucrose or about 1 mg or 2 mg of sucrose to the PCR Master Mix yielded similar amounts of the amplicon products of the 16 loci (FIG. 2). When PCR was performed after about 7 days of storage of the evaporated mixture at ambient temperature (t=7 days), addition of no sucrose to the Master Mix resulted in lower amounts of the amplicon products of the 16 loci compared to addition of about 1 mg or 2 mg of sucrose to the Master Mix (FIG. 3).

Example 4: Preservation of Human Serum Solids in Glycerol

An aqueous solution containing varying amounts of glycerol (0 mg, or about 2.5 mg, 5 mg, 7.5 mg or 10 mg) and an aqueous solution containing varying amounts of sucrose (0 mg, or about 5 mg, 7.5 mg or 10 mg) were added to a volume (about 50 µL) of human serum in natural serum fluid in a tube. The volume of human serum contained about 7.5 mg of serum solids (non-volatile components of serum). Water was removed from the resulting mixture by evaporation at reduced pressure (about 0.2 atm) and ambient temperature for about two days.

Figure 4:
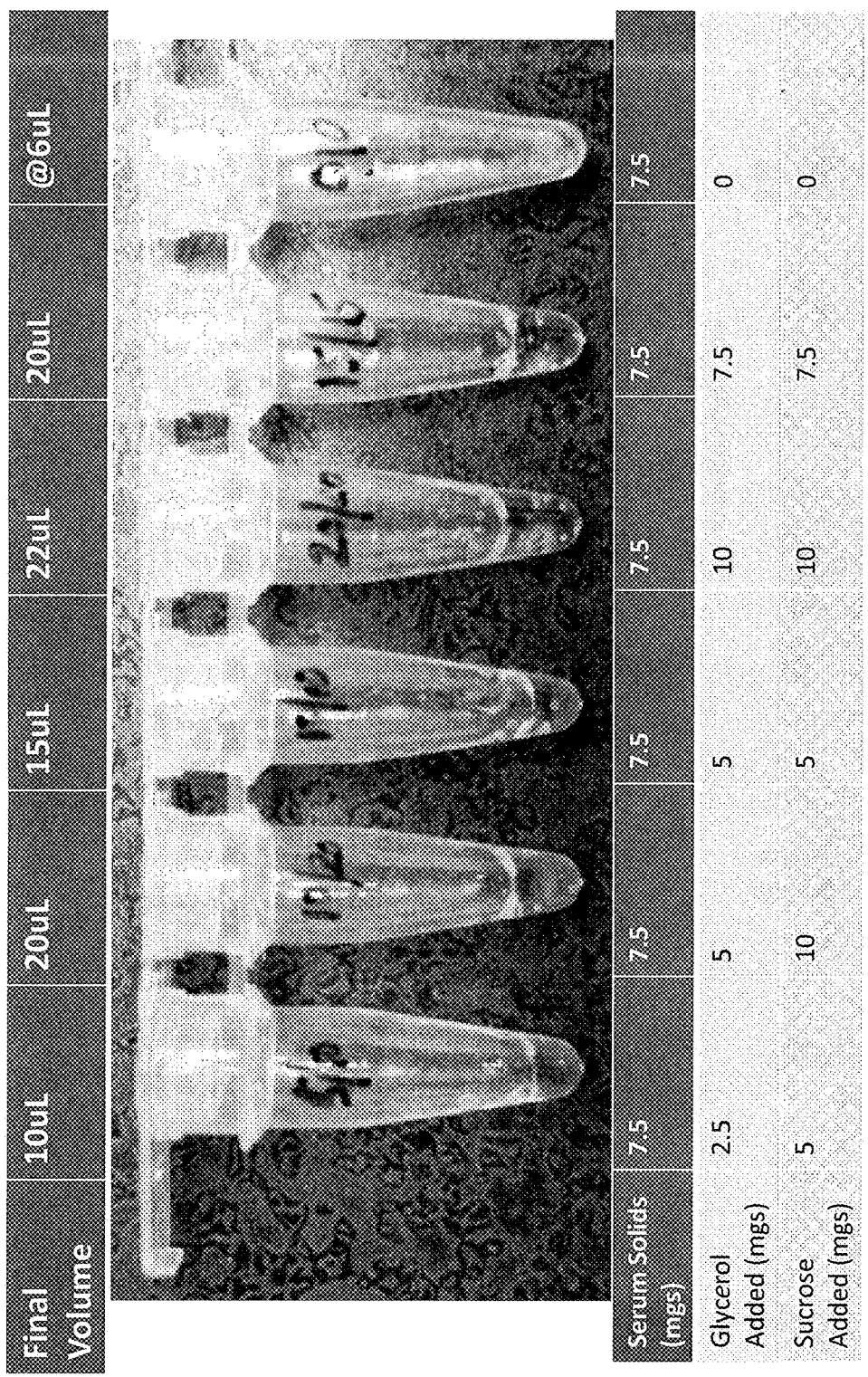
FIG. 4 shows mixtures containing human serum solids and varying amounts of glycerol and sucrose after removal of water under reduced pressure.

FIG. 4 shows the approximate volume of evaporated mixtures containing about 7.5 mg of human serum solids and varying amounts of glycerol and sucrose, after evaporation of water at about 0.2 atm and ambient temperature for about two days. The five evaporated mixtures containing human serum solids and sucrose in glycerol were clear and showed no apparent flocculation or precipitation of serum solids.

Example 5: Preservation of RT-PCR Reagents in Glycerol or Glycerol/1,3-Propanediol for Human 18S rRNA Analysis An undiluted volume (about 25 µL) of the Master Mix of the Ag-Path ID™ One-Step RT-PCR Kit (Life Technologies) for analysis of human 18S ribosomal RNA (rRNA) was placed in a PCR tube. The volume of Master Mix contained some amount (e.g., about 0.5-4 µL) of glycerol. Sucrose (about 2.5 mg), and glycerol (about 1 µL) or 1,3-propanediol (about 1 µL), were added to the Master Mix. Water was removed from the resulting mixture by evaporation at reduced pressure (about 0.2 atm) and ambient temperature overnight to yield a fluid mixture having a volume of about 8 t L. After adding mineral oil (about 1 µL), 1% Triton®-X (about 1 µL of a stock solution diluted 100-fold with distilled water) or 1% Tween®-20 (about 1 µL of a stock solution diluted 100-fold with distilled water), or no additional substance, to the fluid mixture, the mixture was subjected to reduced pressure (about 0.2 atm) at ambient temperature for about two additional hours. The evaporated mixture containing the RT-PCR reagents and sucrose, and optionally mineral oil or a detergent, in glycerol or glycerol/1,3-propanediol was rehydrated for immediate testing or was stored in the PCR tube capped with a snap-on cap at ambient temperature (about 25° C.) for about 7 days before rehydration and testing.

For analysis of human 18S rRNA, nuclease-free water and template RNA (about 10 ng of HeLa total RNA) were added to the evaporated mixture in the PCR tube to a final volume of about 25 µL. Reverse transcription PCR was performed according to the manufacturer's recommended protocol. Production of the target 18S rRNA amplicon product having about 313 base pairs (bp) was analyzed by gel electrophoresis using 2% agarose gel and ethidium bromide for UV visualization.

Figure 5:
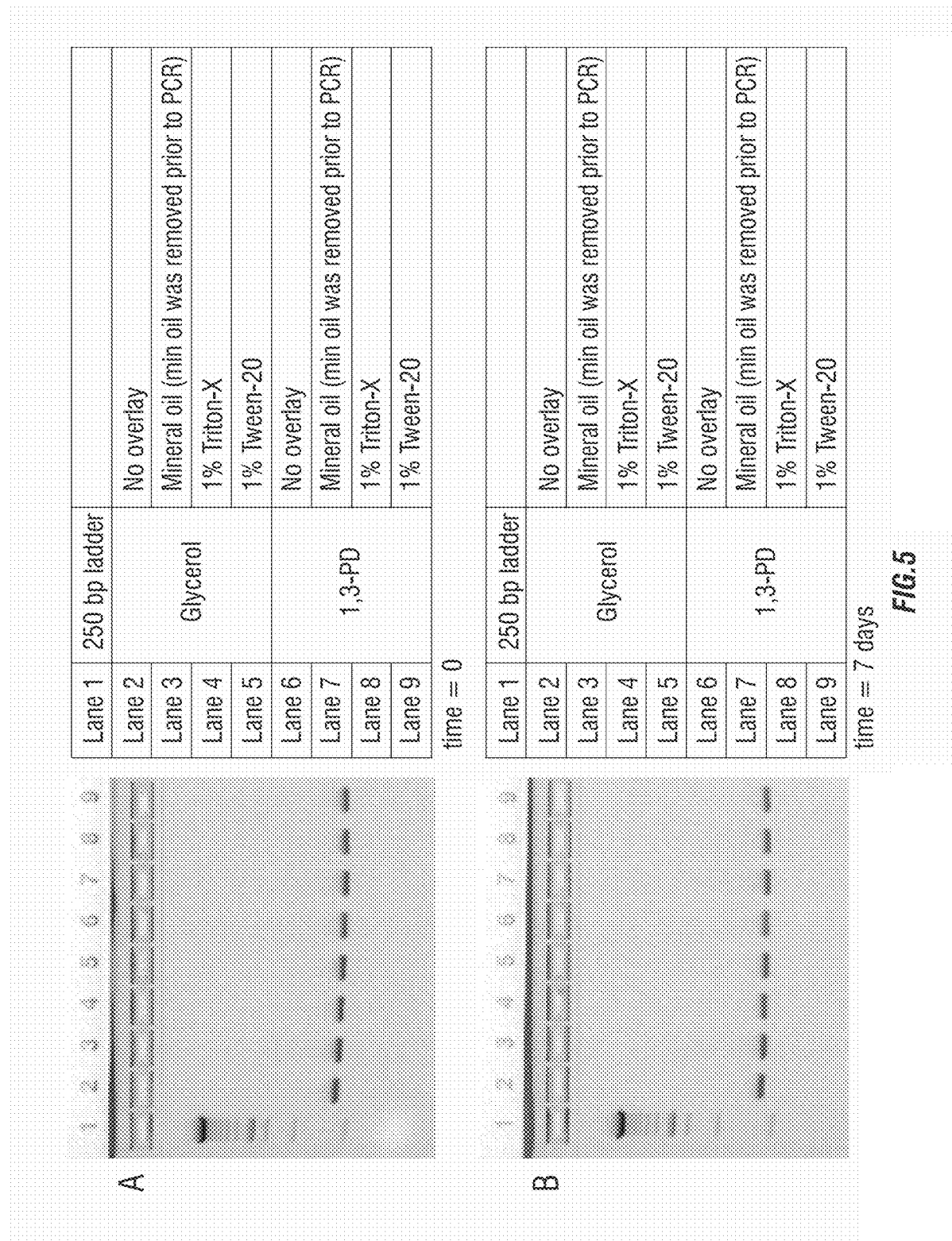
FIG. 5 (A-B) shows a electrophoresis results of RT-PCR analysis of human 18S rRNA performed at time=0 (A) or about 7 days after (B) sucrose and glycerol or 1,3-propanediol, and optionally mineral oil or a detergent, had been added to a master mix of RT-PCR reagents.

Preservation of the reagents was assessed by electrophoresis of the RT-PCR products generated at time=0 or after about 7 days of storage in sucrose and glycerol or 1,3-propanediol ("1,3-PD"), and optionally mineral oil or a detergent, added to the Master Mix (FIGS. 5A and 5B). For the "No overlay" tests, no mineral oil and no detergent had been added to the Master Mix. For the "Mineral oil" tests, mineral oil, but no detergent, had been added to the Master Mix, and the mineral oil was removed before RT-PCR was conducted. For the "1% Triton-X" tests, 1% Triton®-X, but no mineral oil, had been added to the Master Mix. For the "1% Tween-20" tests, 1% Tween®-20, but no mineral oil, had been added to the Master Mix. These results show that RT-PCR generated comparable levels of the target 313 bp 18S rRNA amplicon product at time=0 or about 7 days after sucrose and glycerol or 1,3-propanediol, and optionally mineral oil or a detergent, had been added to the Master Mix.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

The invention being thus described, it will be obvious that the same may be varied in many ways. Such variations are not to be regarded as a departure from the spirit and scope of the inventions.

What is claimed is:

1. A composition comprising:
    a) biological material, comprising a polypeptide, a polynucleotide or a biological sample, or any combination thereof, and wherein said biological material is
        (i) one or more reagents for performing PCR, wherein the reagents for performing PCR comprise a DNA polymerase and at least one pair of a forward primer and a reverse primer for amplifying at least one nucleic acid locus; and the at least one pair of forward primer and reverse primer optionally is labeled with a dye;
        (ii) one or more reagents for performing reverse transcription PCR (RT-PCR), wherein: the reagents for performing RT-PCR comprise a reverse transcriptase, a DNA polymerase, at least one reverse transcription primer for reverse transcribing at least one polyribonucleotide to produce at least one polydeoxyribonucleotide complementary to the at least one polyribonucleotide, and at least one pair of a forward primer and a reverse primer for amplifying the at least one complementary polydeoxyribonucleotide; and wherein the at least one reverse transcription primer optionally is labeled with a dye and the at least one pair of forward primer and reverse primer optionally is labeled with a dye; or
        (iii) one or more reagents for performing an immunoassay, wherein the one or more reagents for performing an immunoassay comprise an antibody that is specific for a target antigen or analyte; the antibody is labeled with a dye or is conjugated to a detection protein or enzyme; and the antibody optionally is bound to a solid substrate; and b) at least one solvent, wherein said solvent or solvents are
(i) at least one alcohol solvent selected from the group consisting of linear and branched C2-C6 acyclic alcohols having one or more hydroxyl groups and C3-C6 cyclic alcohols having one or more hydroxyl groups and three to six ring carbon atoms, wherein the acyclic alcohols and the cyclic alcohols optionally comprise one or more halide atoms; or
(ii) at least one ionic organic solvent comprising an organic salt and an organic hydrogen bond donor, wherein the composition is in a fluid state and is substantially free of water; wherein the at least one alcohol solvent is substantially soluble in water; has a boiling point substantially greater than that of water; and comprises no more than about 10% water by mass; wherein said polypeptide, a polynucleotide or a biological sample, or any combination thereof retains its structural integrity, function, and/or retains its activity after storage.

2. The composition of claim 1, wherein the at least one alcohol solvent comprises ethylene glycol, 1,2-propanediol, 1,3-propanediol, glycerol, 1,2-butanediol, 1,3-butanediol, 1,4-butanediol, 2,3-butanediol, 1,2,4-butanetriol or 1,5-pentanediol, or any combination thereof.

3. The composition of claim 1, wherein the at least one pair of forward and reverse primers comprises at least 5 different pairs of forward and reverse primers for amplifying at least 5 different short tandem repeat (STR) loci utilized in a forensic database, and
wherein each of the at least 5 different pairs of forward and reverse primers optionally is labeled with a dye.

4. The composition of claim 1, further comprising one or more reagents for performing a sandwich immunoassay, wherein the reagents for performing a sandwich immunoassay comprise a first antibody that is specific for a target antigen or analyte and a second antibody that is specific for the target antigen or analyte; said second antibody is labeled with a dye or is conjugated to a detection protein or enzyme; and the first antibody optionally is bound to a solid substrate.

5. The composition of claim 1, wherein said biological material comprises:
a) whole or fractionated animal blood;
b) whole or fractionated animal plasma; or
c) whole or fractionated animal serum.

6. The composition of claim 1, wherein said biological material comprises animal cells, mammalian cells, human cells, plant cells, microbial cells, pathogenic cells, bacterial cells, fungal cells, protozoan cells or viral particles, or any combination thereof, or lysates or extracts thereof.

7. The composition of claim 1, further comprising one or more substances selected from the group consisting of reducing agents, antioxidants, free radical scavengers, oxygen radical scavengers, hydroxyl radical scavengers, singlet oxygen quenchers, hydroperoxide-removing agents, protease inhibitors, nuclease inhibitors, ribonuclease (RNase) inhibitors, deoxyribonuclease (DNase) inhibitors, metal chelators, preservatives, anti-microbials, buffers (or buffering agents), detergents, chaotropes, $M^{+1}$ salts, and $M^{+2}$ salts.

8. The composition of claim 1, wherein said biological material is stable, retains its function, and/or retains its activity after storage at ambient temperature for at least about 2 weeks or 1 month.

9. A method of preserving a biological material, comprising:
b) a) mixing an aqueous mixture comprising the biological material with at least one solvent, wherein said biological material is
(i) one or more reagents for performing PCR, wherein the reagents for performing PCR comprise a DNA polymerase and at least one pair of a forward primer and a reverse primer for amplifying at least one nucleic acid locus; and the at least one pair of forward primer and reverse primer optionally is labeled with a dye;
(ii) one or more reagents for performing reverse transcription PCR (RT-PCR), wherein: the reagents for performing RT-PCR comprise a reverse transcriptase, a DNA polymerase, at least one reverse transcription primer for reverse transcribing at least one polyribonucleotide to produce at least one polydeoxyribonucleotide complementary to the at least one polyribonucleotide, and at least one pair of a forward primer and a reverse primer for amplifying the at least one complementary polydeoxyribonucleotide; and wherein the at least one reverse transcription primer optionally is labeled with a dye and the at least one pair of forward primer and reverse primer optionally is labeled with a dye; or
(iii) one or more reagents for performing an immunoassay, wherein the one or more reagents for performing an immunoassay comprise an antibody that is specific for a target antigen or analyte; the antibody is labeled with a dye or is conjugated to a detection protein or enzyme; and the antibody optionally is bound to a solid substrate; and
wherein said solvent or solvents are
(iv) at least one alcohol solvent selected from the group consisting of linear and branched C2-C6 acyclic alcohols having one or more hydroxyl groups and C3-C6 cyclic alcohols having one or more hydroxyl groups and three to six ring carbon atoms, wherein the acyclic alcohols and the cyclic alcohols optionally comprise one or more halide atoms; or
(v) at least one ionic organic solvent comprising an organic salt and an organic hydrogen bond donor; and
b) removing water from the aqueous organic mixture to produce a composition comprising the biological material, and the at least one alcohol solvent, wherein the composition is in a fluid state and is substantially free of water.

10. The method of claim 9, wherein the at least one solvent is substantially soluble in water; has a boiling point substantially greater than that of water; and comprises no more than about 10% water by mass.

11. The method of claim 9, wherein said removing water from the aqueous organic mixture comprises evaporation.

12. The method of claim 9, wherein said removing water from the aqueous organic mixture does not produce, include, or involve an intermediate solid state.

13. The composition of claim 1, wherein the at least one ionic organic solvent is a eutectic solvent.

14. The composition of claim 1, wherein the molar ratio of the organic salt to the organic hydrogen bond donor in the at least one ionic organic solvent is from about 1:1 to about 1:2.

15. The composition of claim 1, wherein the organic salt of the at least one ionic organic solvent comprises one or more organic salts selected from the group consisting of primary ammonium salts, secondary ammonium salts, tertiary ammonium salts, and quaternary ammonium salts.

16. The composition of claim 15, wherein the organic salt comprises a choline salt.

17. The composition of claim 1, wherein the organic hydrogen bond donor of the at least one ionic organic solvent comprises one or more organic hydrogen bond donors selected from the group consisting of urea compounds, thiourea compounds, carbamates, amides, carboxylic acids, phenolic compounds, acyclic alcohols, and cyclic alcohols.

18. The composition of claim 17, wherein the organic hydrogen bond donor comprises urea, acetamide, citric acid, malonic acid, oxalic acid, ethylene glycol, 1,2-propanediol, 1,3-propanediol, glycerol, 1,2-butanediol, 1,3-butanediol, 1,4-butanediol, 2,3-butanediol, 1,2,4-butanetriol or 1,5-pentanediol, or any combination thereof.

19. A container comprising the composition of claim 1.

* * * * *